(12) United States Patent
Havlicek et al.

(10) Patent No.: US 9,957,273 B2
(45) Date of Patent: May 1, 2018

(54) 5-SUBSTITUTED 7-[4-(2-PYRIDYL)PHENYLMETHYLAMINO]-3-ISOPROPYLPYRAZOLO4,3-D]PYRIMIDINE DERIVATIVES, USE THEREOF AS MEDICAMENTS, AND PHARMACEUTICAL COMPOSITIONS

(71) Applicant: USTAV EXPERIMENTALNI BOTANIKY AV CR, V.V.I., Prague (CZ)

(72) Inventors: Libor Havlicek, Prague (CZ); Antonin Sturc, Prague (CZ); Vladimir Krystof, Olomouc (CZ); Radek Jorda, Olomouc (CZ); Tomas Pospisil, Olomouc (CZ); Stefan Zahler, Maisach (DE); Angelika Vollmar, Pullach (DE); Miroslav Strnad, Olomouc (CZ)

(73) Assignee: USTAV EXPERIMENTALNI BOTANIKY AV CR, V.V.I., Prague (CZ)

( * ) Notice: Subject to any disclaimer, the term of this patent is extended or adjusted under 35 U.S.C. 154(b) by 0 days. days.

(21) Appl. No.: 15/558,151

(22) PCT Filed: Oct. 2, 2015

(86) PCT No.: PCT/CZ2015/050006
§ 371 (c)(1),
(2) Date: Sep. 13, 2017

(87) PCT Pub. No.: WO2016/180380
PCT Pub. Date: Nov. 17, 2016

(65) Prior Publication Data
US 2018/0072736 A1    Mar. 15, 2018

(30) Foreign Application Priority Data

May 14, 2015    (CZ) .................................... 2015-324

(51) Int. Cl.
C07D 487/04    (2006.01)

(52) U.S. Cl.
CPC ................................ C07D 487/04 (2013.01)

(58) Field of Classification Search
CPC .................................................. C07D 487/04
See application file for complete search history.

(56) References Cited

FOREIGN PATENT DOCUMENTS

| EP | 1475094 A1 | 11/2004 |
|---|---|---|
| WO | 2010139288 A1 | 12/2010 |

OTHER PUBLICATIONS

International Search Report and Written Opinion for corresponding PCT Application No. PCT/CZ2015/050006, dated Jan. 27, 2016.

*Primary Examiner* — Rebecca L Anderson
(74) *Attorney, Agent, or Firm* — Notaro, Michalos & Zaccaria P.C.

(57) ABSTRACT

5-substituted-7-[4-(2-pyridyl)phenylmethylamino]-3-isopropylpyrazolo[4,3-d]pyrimidines are potent inhibitors of protein kinases, especially cyclin-dependent kinases such as CDK2 and CDK5, and display antileukemic, pro-apoptotic, antiangiogenic and anticancer activities. The invention also relates to processes for their preparation, to pharmaceutical compositions and to their use as medicaments, particularly in the treatment of disorders involving cell proliferation, apoptosis, angiogenesis and inflammation, such as leukemia and metastatic solid cancer.

8 Claims, 3 Drawing Sheets

5-SUBSTITUTED 7-[4-(2-PYRIDYL)PHENYLMETHYLAMINO]-3-ISOPROPYLPYRAZOLO4,3-D]PYRIMIDINE DERIVATIVES, USE THEREOF AS MEDICAMENTS, AND PHARMACEUTICAL COMPOSITIONS

FIELD OF THE INVENTION

The present invention relates to 5-substituted 7-[4-(2-pyridyl)phenylmethylamino]-3-isopropylpyrazolo[4,3-d]pyrimidines, to processes for their preparation, to pharmaceutical compositions comprising these derivatives and to their use in the treatment of disorders, such as leukemia and metastatic solid cancer.

BACKGROUND ART

The CDKs are a family of serine/threonine protein kinases that are classified as regulators of the cell cycle (CDK1, 2, 4, 6) or transcription (CDK7, 8, 9, 11, 20). However, in the last years they have been shown to participate also in angiogenesis, senescence, exocytosis, spermatogenesis, and neuronal development (Malumbres M. Genome Biol 2014; 15:122). CDK activity is dependent on the binding of regulatory subunits called cyclins, which are produced and degraded during different phases of the cell cycle. The timing of CDK activity is also subject to negative regulation mediated by the binding of natural CDK inhibitors (INK4, Cip/Kip), and by inhibitory phosphorylation catalyzed by the Wee1 and Myt1 kinases, which can be reversed by the cdc25 phosphatases (Pavletich N P, J Mol Biol 1999; 287: 821-828; Boutros and Duccomun, Cell Cycle 2008; 7:401-406).

The uncontrolled upregulation of CDK activity has been identified as a hallmark of cancer and there are several mechanisms described to cause CDK hyperactivity. Loss of function mutations (deletions, silencing, or point mutations) affecting natural CDK inhibitors as well as an overexpression of CDK-activating cyclins are common ways of such deregulation. Besides that, an excessive production of cyclin D1 was detected in breast, bladder, esophageal and squamous cell carcinoma, cyclin E in colon, lung and breast cancers and in some leukemias, or cyclin A in lung carcinoma (Hall and Peters, Adv Cancer Res 1996; 68:67-108; Leach et al, Cancer Res 1993; 53:1986-1989; Dobashi et al, Am J Pathol 1998; 153:963-972; Keyomarsi et al, Oncogene 1995; 11:941-950; Iida et al, Blood 1997; 90:3707-3713). However, in some cases, especially those involving CDK4 and 6, hyperactivity is caused by the amplification or overexpression of the CDK gene itself (Nagel et al, Leukemia 2008; 22:387-392, Faussillon et al, Cancer Lett 2005; 221: 67-75, Tang et al., Clin Cancer Res 2012; 18:4612-4620).

Alternatively, non-mitotic CDKs have been also found to be implicated in cellular transformation and/or cancer phenotype. Notable example is CDK9, a kinase that regulates elongational phase of mRNA transcription by phosphorylation of C-terminus of RNA polymerase II. It has been well documented that many cancer types, including leukemias, are heavily dependent on continuous expression of anti-apoptotic and pro-survival genes such as Mcl-1 or survivin (Chen et al, Blood 2005, 106, 2513; McMillin et al, Br. J. Haematol. 2011, 152, 420). Another example is CDK5, a kinase that regulates cellular migration; it has been found to be hyperactivated in some human cancers and promotes their metastasis (Eggers et al, Clin Cancer Res. 2011; 17(19):6140-5). In addition, CDK5 is highly expressed and active in proliferating endothelial cells (J Cell Biochem. 2004; 91(2): 398-409) and its function in these cells is linked to their migration and sprouting and promotes angiogenesis (Liebl et al, J Biol Chem. 2010; 285(46):35932-43).

For these reasons, CDKs and their natural binding partners have become important targets for anticancer drug development. Most medicinal programmes in this area have focused on small molecule inhibitors. Most known CDK inhibitors are pan-selective and they block the transcriptional regulators CDK7 and CDK9 in addition to the cell cycle regulating CDK1, CDK2 and CDK4. These compounds induce cell cycle arrest and activate apoptosis by inhibiting transcription, which is most effective in cells that are strongly dependent on the expression of antiapoptotic proteins with short half-lives such as Mcl-1. Many groups have demonstrated that early inhibitors such as roscovitine and flavopiridol are effective against multiple myeloma and other malignancies that depend on continuous mRNA synthesis and Mcl-1 expression (Raje et al, Blood 2005; 106: 1042-1047; Gojo et al, Clin Cancer Res 2002; 8:3527-3538). Inhibitors of the transcriptional CDKs also influence the stabilization of the tumor suppressor p53, probably by downregulating its target genes; these include the ubiquitin ligase Mdm2, which negatively regulates p53 (Dai and Lu, J Biol Chem 2004; 279:44475-44482). Based on in vitro studies, simultaneous inhibition of several CDKs (i.e. CDK1, 2 and 9) has been proposed as a viable strategy for selecting clinical drug candidates (Cai et al, Cancer Res 2006; 66:9270-9280).

It has been shown that inhibition of CDK5 results in the suppression of cancer growth and metastatic progression in preclinical models of pancreatic and breast cancer (Feldman et al, Cancer Res. 2010; 70(11):4460-9; Feldman et al, Cancer Biol Ther. 2011; 12(7):598-609; Liang et al, Sci Rep. 2013; 3:2932). At the molecular level, CDK5 is essential for TGF-b-induced epithelial-mesenchymal transition and breast cancer progression (Liang et al, Sci Rep. 2013; 3:2932). In addition, inhibition of CDK5 in endothelial cells also suppresses angiogenesis (Liebl et al., J Biol Chem. 2010; 285(46):35932-43; Liebl et al., Angiogenesis. 2011; 14(3):281-91). In leukemic cells, CDK5 has been found to phosphorylate Noxa, a BH3-only member of the Bcl-2 family, and its inhibition promoted apoptosis (Lowman et al, Mol Cell 2010; 40(5):823-33).

It is an object of this invention to provide new, very potent anticancer, antileukemic, and antiangiogenic compounds.

DISCLOSURE OF THE INVENTION

Object of the present invention are 5-substituted 7-[4-(2-pyridyl)phenylmethylamino]-3-isopropylpyrazolo[4,3-d] pyrimidines of the general formula I

I wherein,

R is selected from the group containing heterocycloalkyl, which is a $C_3$-$C_{10}$ cycloalkyl group wherein one or more, preferably 1 to 3, of the ring carbons is/are replaced with a heteroatom selected from N, O, S, said heterocycloalkyl group being optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl, and amino substituents;

heterocycloalkyl alkyl, which is a $C_3$-$C_{10}$ cycloalkyl group wherein one or more, preferably 1 to 3, of the ring carbons is/are replaced with a heteroatom selected from N, O, S, bound via a $C_1$-$C_4$ alkylene spacer, more preferably via a $C_2$-$C_3$ alkylene spacer, said heterocycloalkyl alkyl group being optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl and amino substituents;

R'—X wherein X is selected from —NH— and —N($C_1$-$C_8$ alkyl)- moiety, and

R' is selected from $C_2$-$C_{10}$ linear or branched alkyl, optionally substituted by at least one substituent selected from hydroxy and amino substituents, preferably by one hydroxy and/or one amino substituent;

(dialkylamino)alkyl group wherein the alkyls are independently selected from $C_1$-$C_{10}$ linear or branched alkyl;

$C_3$-$C_{10}$ cycloalkyl, which is a cyclic or polycyclic alkyl group containing 3 to 10 carbon atoms, optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl and amino substituents;

heterocycloalkyl, which is a $C_3$-$C_{10}$ cycloalkyl group wherein one or more, preferably 1 to 3, of the ring carbons is/are replaced with a heteroatom selected from N, O, S, said heterocycloalkyl group being optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl and amino substituents;

heterocycloalkyl alkyl, which is a $C_3$-$C_{10}$ cycloalkyl group wherein one or more, preferably 1 to 3, of the ring carbons is/are replaced with a heteroatom selected from N, O, S, bound via a $C_1$-$C_4$ alkylene spacer, more preferably via a $C_2$-$C_3$ alkylene spacer, said heterocycloalkyl alkyl group being optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl and amino substituents;

benzyl group, optionally substituted independently at each occurrence by at least one substituent selected from the group consisting of fluoro, chloro, hydroxy, $C_1$-$C_4$ alkyl, $C_1$-$C_4$ alkoxy, $C_1$-$C_4$ hydroxyalkyl and amino substituents;

and pharmaceutically acceptable salts thereof, in particular salts with alkali metals, ammonium or amines, or addition salts with acids.

Preferably, the $C_2$-$C_{10}$ linear or branched alkyl is selected from the group containing propyl, isopropyl, butyl, isobutyl, tert-butyl, pentyl, isopentyl, hexyl, heptyl, octyl, and nonyl.

In another preferred embodiment, the $C_2$-$C_{10}$ linear or branched alkyl substituted by hydroxy is selected from the group containing 2-hydroxyethyl, 2(RS, R or S)-hydroxypropyl, 3-hydroxypropyl, 4-hydroxybut-2(RS, R, or S)-yl, 2-hydroxy-2-methylpropyl, 3-hydroxy-3-methylbutyl, 2,3-dihydroxypropyl, 1-hydroxy-3-methylbut-2-yl, and (3RS)-2-hydroxypent-3-yl.

In yet another preferred embodiment, the $C_2$-$C_{10}$ linear or branched alkyl substituted by amino is selected from the group containing 2-aminoethyl, 3-aminopropyl, 4-aminobutyl, 5-aminopentyl, 6-aminohexyl.

In a further preferred embodiment, the $C_2$-$C_{10}$ linear or branched alkyl substituted by amino and hydroxy is 3-amino-2-hydroxypropyl.

In one preferred embodiment, the (dialkylamino)alkyl group is selected from the group consisting of (dimethylamino)methyl, 2-(dimethylamino)ethyl, 3-(dimethylamino)propyl, 4-(dimethylamino)butyl, (diethylamino)methyl, 2-(diethylamino)ethyl, 3-(diethylamino)propyl, 4-(diethylamino)butyl.

In another preferred embodiment, the $C_3$-$C_{10}$ cycloalkyl is selected from the group containing cyclopropyl, cyclobutyl, cyclopentyl, cyclohexyl.

In yet another preferred embodiment, the $C_3$-$C_{10}$ cycloalkyl is selected from the group containing trans-4-aminocyclohexyl, cis-4-aminocyclohexyl, cis/trans-4-aminocyclohexyl, cis-2-aminocyclohexyl, trans-2-aminocyclohexyl, cis, trans-2-aminocyclohexyl, 3-aminocyclohexyl, cis, trans-4-hydroxycyclohexyl.

In another preferred embodiment, the heterocycloalkyl is selected from the group containing N-morpholinyl, N-pyrrolidinyl, N-pyrazolidinyl, N-imidazolidinyl, N-piperazinyl, N-piperidinyl, N-thiomorpholinyl, 4-methylpiperazin-1-yl, 4-(2-hydroxyethyl)piperazin-1-yl.

The substituted benzyl is preferably selected from the group containing 2-methoxybenzyl, 3-methoxybenzyl, 4-methoxybenzyl, 3,5-dimethoxybenzyl, 2,6-dimethoxybenzyl, 2,4,6-trimethoxybenzyl, 3,4,5-trimethoxybenzyl, 2-fluorobenzyl, 3-fluorobenzyl, 4-fluorobenzyl, 2-chlorobenzyl, 3-chlorobenzyl, and 4-chlorobenzyl.

In one preferred embodiment, the heterocycloalkyl alkyl group is selected from the group consisting of (aziridin-1-yl)ethyl, (azetidin-1-yl)ethyl, (azolidin-1-yl)ethyl, (piperidin-1-yl)ethyl, (aziridin-1-yl)propyl, (azetidin-1-yl)propyl, (azolidin-1-yl)propyl, and (piperidin-1-yl)propyl.

When chiral centers are present in the molecule, the present invention encompasses all optically active isomers, their mixtures and racemates. In particular, the compounds of general formula I, having independently at each occurrence (R) or (S) configuration in R are encompassed by this invention.

The 5-substituted-7-[4-(2-pyridyl)phenylmethylamino]-3-isopropylpyrazolo[4,3-d]pyrimidines of the general formula I are suitable for use as medicaments. In particular, they are useful in inhibiting aberrant cell proliferation and/or inducing apoptosis.

In one embodiment, the 5-substituted-7-[4-(2-pyridyl)phenylmethylamino]-3-isopropylpyrazolo[4,3-d]pyrimidines of the general formula I are useful in inhibiting angiogenesis, in particular tumor angiogenesis.

In another embodiment, the 5-substituted-7-[4-(2-pyridyl)phenylmethylamino]-3-isopropylpyrazolo[4,3-d]pyrimidines of the general formula I are useful in the treatment of cancer disorders. In particular, these compounds possess combined antiproliferative, antiangiogenic, antiinflammatory and proapoptotic activities. More specifically, the compounds of general formula I show activity in the treatment of animal and human leukemia, metastatic cancer disorders—solid tumors.

In yet another embodiment, the 5-substituted-7-[4-(2-pyridyl)phenylmethylamino]-3-isopropylpyrazolo[4,3-d]pyrimidines of the general formula I are useful for inhibition of the kinase CDK5 which is one of the key components involved in regulation of endothelial cell migration via cell adhesion, the microtubule and the actin cytoskeleton formation. CDK5 inhibition is also involved in the lamellipodium formation as a prerequisite for proper cell migration.

Thus, the 5-substituted-7-[4-(2-pyridyl)phenylmethylamino]-3-isopropylpyrazolo[4,3-d]pyrimidines of the general formula I are useful for inhibiting mammalian endothelial cell migration, in particular for inhibiting and/or treatment of vascularization in cancers. They are suitable for inhibition and/or treatment of vascularization during cancer development, embryonic development, menstruation cycle and wound healing.

Another object of this invention is a method of treatment of disorders involving aberrant cell proliferation and/or apoptosis and/or endothelial cell migration, such as cancer (e.g., leukemia, metastatic cancers, solid tumors), vascularization during cancer and embryonic development, menstruation cycle and wound healing in a mammal in need of such treatment by administering a therapeutically effective amount of at least one compound of formula I to the mammal.

The invention also encompasses a pharmaceutical composition, which comprises at least one 5-substituted-7-[4-(2-pyridyl)phenylmethylamino]-3-isopropylpyrazolo[4,3-d]pyrimidine of the general formula I, and a pharmaceutically acceptable carrier.

In a preferred embodiment, the derivatives of general formula I bear substituent R selected from the group comprising: N-morpholinyl, N-pyrrolidinyl, N-pyrazolidinyl, N-imidazolidinyl, N-piperazinyl, N-piperidinyl, N-thiomorpholinyl, 4-methylpiperazin-1-yl, 4-(2-hydroxyethyl)piperazinyl, (R)-(2-hydroxymethylpyrrolidin-1-yl), ethylamino, propylamino, butylamino, (2-hydroxyethyl)amino, (3-hydroxypropyl)amino, 2(R)-hydroxypropylamino, 2(S)-hydroxypropylamino, 4-hydroxybut-2(R)-ylamino, 4-hydroxybut-2(S)-ylamino, 4-hydroxybut-2(R,S)-ylamino, 2-(hydroxy-2-methyl)propylamino, (2,3-dihydroxypropyl)amino, (1-hydroxy-3-methylbutyl)amino, [(R,S)-(2-hydroxypent-3-yl)]amino, [(R)-(2-hydroxypent-3-yl)]amino, [(S)-(2-hydroxypent-3-yl)]amino, (R)-[1-isopropyl-2-hydroxyethyl]amino, (S)-[1-isopropyl-2-hydroxyethyl]amino, (2-aminoethyl)amino, (3-aminopropyl)amino, (4-aminobutyl)amino, (5-aminopentyl)amino, (6-aminohexyl)amino, [3-amino-2-hydroxypropyl]amino, [1-(dimethylamino)methyl]amino, [2-(dimethylamino)ethyl]amino, [3-(dimethylamino)propyl]amino, [4-(dimethylamino)butyl]amino, [2-(diethylamino)ethyl]amino, [3-(diethylamino)propyl]amino, (aziridin-1-yl)ethylamino, (azolidin-1-yl)ethylamino, (azetidin-1-yl)ethylamino, (piperidin-1-)ethylamino, (azetidin-1-yl)ethylamino, (azetidin-1-yl)propylamino, cyclopropylamino, cyclobutylamino, cyclopentylamino, cyclohexylamino, (cis-2-aminocyclohexyl)amino, (trans-2-aminocyclohexyl)amino, (cis, trans-2-aminocyclohexyl)amino, (cis, trans-3-aminocyclohexyl)amino, (trans-4-aminocyclohexyl)amino, (cis-4-aminocyclohexyl)amino, (cis, trans-4-aminocyclohexyl)amino, (cis-2-hydroxycyclohexyl)amino, (trans-2-hydroxycyclohexyl)amino, (cis, trans-2-hydroxycyclohexyl)amino, (cis, trans-3-hydroxycyclohexyl)amino, (trans-4-hydroxycyclohexyl) amino, (cis-4-hydroxycyclohexyl)amino, (cis, trans-4-hydroxycyclohexyl)amino, (2-methoxybenzyl)amino, (3-methoxybenzyl)amino, (4-methoxybenzyl)amino, (3,5-dimethoxybenzyl)aminoe, (2,6-dimethoxybenzyl)amino, (3,4,5-trimethoxybenzyl)amino, (2,4,6-trimethoxybenzyl)amino, (2-fluorobenzyl)amino, (3-fluorobenzyl)amino, (4-fluorobenzyl)amino, (2-chlorobenzyl)amino, (3-chlorobenzyl)amino, (4-chlorobenzyl)amino, (2,4-dichlorobenzyl)amino, (3,4,5-trichlorobenzyl)amino.

Processes of Preparation of Compounds of General Formula I

The pyrazolo[4,3-d]pyrimidines of the formula I according to the present invention, having various substituents at the position 5 of the heterocycle, may be prepared via intermediate compounds using the procedures outlined in Scheme 1. The procedure includes the steps of oxidation of methylsulfanyl group to methylsulfonyl and of nucleophilic substitution of chloro atom at the position 7 of the heterocycle. The nucleophilic substitution into position 7 can be carried out under moderate conditions with a high yield. The last reaction step, i.e. the nucleophilic substitution into position 5 (conversion of compound 7 to final compounds 8), requires harsh conditions (150 to 160° C./1 to 20 h). The final compounds have to be isolated by column chromatography.

Scheme 1. Scheme of synthesis.

Pharmaceutical Compositions

Suitable routes for administration include oral, rectal, topical (including dermal, ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutical composition comprises about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of convectional mixing, granulating, coating, dissolving or lyophilising processes.

Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of convectional dissolving or lyophilising processes. The solutions or suspensions mentioned can comprise viscosity-increasing substances, such as sodium carboxymethylcellulose, carboxymethylcellulose, dextran, polyvinylpyrrolidone or gelatin.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Hills AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients. Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatin and soft, closed capsules of gelatin and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities. Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilisers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists of, in particular, hydrocarbons, for example vaseline, paraffin oil or hard paraffins, which preferably comprise suitable hydroxy compounds, such as fatty alcohols or esters thereof, for example cetyl alcohol or wool wax alcohols, such as wool wax, to improve the water-binding capacity. Emulsifiers are lipophilic substances, such as sorbitan fatty acid esters (Spans), preferably sorbitan oleate or sorbitan isostearate. Additives to the aqueous phase are, for example, humectants, such as polyalcohols, for example glycerol, propylene glycol, sorbitol and polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or hydrogenated oils, for example hydrogenated groundnut or castor oil, and furthermore fatty acid partial esters of glycerol, for example glycerol mono- and distearate. They also contain e.g. fatty alcohols, emulsifiers and additives mentioned in connection with ointments which increase the uptake of water.

Creams are oil-in-water emulsions, which comprise more than 50% of water. Oily bases used are, in particular, fatty alcohols, for example isopropyl myristate, wool wax, beeswax, or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric fatty acid esters or polyethylene sorbitan fatty acid esters or acidic polyglyceric fatty acid esters (Tween), and furthermore polyoxyethylene fatty alcohol ethers or polyoxyethylene fatty acid esters, or ionic emulsifiers, such as alkali metal salts of fatty alcohol sulphates, preferably sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and polyethylene glycols, and furthermore preservatives and odoriferous substances.

Pastes are creams or ointments containing secretion-absorbing powder constituents, such as metal oxides, for example titanium oxide or zinc oxide, and in addition talc or aluminium silicates, which have the task of binding the moisture or secretions present.

Foams are administered from pressurised containers and they are liquid oil-in-water emulsions present in aerosol foam. As the propellant gases halogenated hydrocarbons, such as polyhalogenated alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments, and the additives mentioned there are likewise used.

Tinctures and solutions usually comprise an aqueous-ethanolic base to which, humectants for reducing evaporation, such as polyalcohols, for example glycerol, glycols and polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives are admixed.

This invention further provides veterinary preparations containing at least one active ingredient together with a veterinary carrier. Veterinary carriers are materials for the application of a composition and include solid, liquid or gaseous substances, which are inert or acceptable in veterinary medicine and are compatible with the active ingredient. These veterinary preparations can be administered orally, parenterally or by any other desired way.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered for a body weight of about 70 kg.

BRIEF DESCRIPTION OF DRAWINGS

FIGS. 1A, B, C and D show the effect of selected novel compounds on the cell cycle of MCF7 cancer cell line.

FIGS. 2A and B show the effect of novel compounds on apoptosis in K562 cells. Activities of caspases 3 and 7 were measured in lysed K562 cells treated with several novel compounds for 24 hours (A) and with increasing doses of compound 33 (B).

EXAMPLES OF CARRYING OUT THE INVENTION

The following examples serve to illustrate the invention without limiting the scope thereof.

Melting points were determined on a Kofler block and are uncorrected. Reagents were from standard commercial sources of analytical grade. Thin layer chromatography (TLC) was carried out using aluminium sheets with silica gel $F_{254}$ from Merck. Spots were visualized under UV light (254 nm). ESI or mass spectra were determined using a Waters Micromass ZMD mass spectrometer (direct inlet, coin voltage 20 V). Column chromatography was performed using Merck silica gel Kieselgel 60 (230-400 mesh). All compounds gave satisfactory elemental analyses (0.4%).

Example 1

3-Isopropyl-7-[4-(2-pyridyl)benzyl]amino-1(2)H-pyrazolo[4,3-d]pyridine (2)

A solution of 7-chloro-3-isopropyl-1 (2)H-pyrazolo[4,3-d]pyridine (1), 1-[4-(pyridin-2-yl)phenyl]methanamine (0.31 g, 1.58 mmol) and ethyldiisopropylamine (0.4 mL, 2.3 mmol) in $CHCl_3$/t-BuOH (6 mL/1 mL) was heated for 1 h at 60° C. After cooling to room temperature the reaction mixture was concentrated under vacuum and the residue was partitioned between $H_2O$ and $CHCl_3$. The combined organic phase was dried with magnesim sulfate and evaporated. Column chromatogr. stepwise 1%, 2%, and 4% MeOH in $CHCl_3$ afforded (after evaporation under vacuum) noncrystalizable amorphous colorless glass form, yield 81% (0.442 g).

ESI+ m/z 345.1 [M+H]$^+$, ESI– m/z 343.1 [M–H]$^-$. $^1$H (500 MHz; DMSO-d$_6$): 1.33 (d, J=7.03 Hz, 6H, —CH—(CH$_3$)$_2$); 3.29 (m, 1H, —CH—(CH$_3$)$_2$); 4.78 (bs, 2H, —NH—CH$_2$—); 7.27-7.29 (m, 1H, ArH); 7.46 (d, J=7.03 Hz, 2H, ArH); 7.80-7.83 (m, 1H); 7.87-7.89 (m, 2H, ArH, —NH—); 8.03 (d, J=7.03 Hz, 2H, ArH); 8.21 (bs, 1H, ArH); 8.60 (d, J=4.28 Hz, 1H, ArH); 12.26 (bs, 1H, —NH—). $^{13}$C (125 MHz; DMSO-d6): 22.2, 26.8, 43.6, 120.6, 122.4, 123.0, 126.9, 127.1, 128.5, 128.8, 137.7, 138.1, 139.4, 140.3, 149.6, 150.0, 150.7, 151.2, 156.3.

Example 2

3-Isopropyl-5-methylsulfanyl-7-[4-(2-pyridyl)benzyl]amino-1(2)H-pyrazolo[4,3-d]pyridine (5)

7-Chloro-3-isopropyl-5-methylsulfanyl-1(2)H-pyrazolo[4,3-d]pyridine (4) (0.56 g, 2.3 mmol), 1-[4-(pyridin-2-yl)phenyl]methanamine (0.48 g, 2.6 mmol) and ethyldiisopropylamine (0.86 mL, 5 mmol) in 12 mL t-BuOH were heated with stirring at 70° C. for 2 h. After cooling to room temperature the reaction mixture was concentrated under vacuum and the residue was partitioned between $H_2O$ and $CHCl_3$. The combined organic phase was dried with magnesim sulfate and evaporated. Crystallization from $CHCl_3$/$Et_2O$ afforded colorless product mp 170-173° C., Yield 87%, (0.79 g).

ESI+ m/z 391.1 [M+H]$^+$, ESI– m/z 389.1 [M–H]$^-$. $^1$H (500 MHz; DMSO-d$_6$): 1.36 (d, J=7.03 Hz, 6H, —CH—(CH$_3$)$_2$); 2.43 (s, 3H, —CH$_3$); 3.31-3.35 (m, 1H, —CH—(CH$_3$)$_2$); 4.75 (bs, 2H, —NH—CH$_2$—); 7.32 (ddd, J=7.34 Hz, J=4.89 Hz, J=0.92 Hz, 1H, ArH); 7.48 (d, J=7.03 Hz, 2H, ArH); 7.84 (dt, J=7.64 Hz, J=1.53 Hz, 1H, ArH); 7.92 (d, J=7.95 Hz, 1H, ArH); 8.05 (bd, J=7.03 Hz, 2H, ArH); 8.63 (bd, J=4.58 Hz, 1H, ArH).

Example 3

7-Chloro-3-isopropyl-5-methylsulfonyl-1(2)H-pyrazolo[4,3-d]pyridine (6)

Solution of Oxone$^R$ (monopersulfate comp., Aldrich Cat: 22,803-6, 36 g) in water (180 mL) was dropped within 1 h to a solution of 7-chloro-3-isopropyl-5-methylsulfanyl-1(2)H-pyrazolo[4,3-d]pyridine (4) (10 g, 41.3 mmol) in EtOH (180 mL) at temperature 55° C. The reaction mixture was stirred for another 1 h at 60° C. After cooling to room temperature, the EtOH was removed by evaporation and the residue was partitioned between $H_2O$ and EtOAc. The combined organic phase was dried with sodium sulfate. Crystallization from EtOAc/$Et_2O$ afforded product mp 111-114° C., yield 81%, (9.17 g).

ESI– m/z 273.1 [M–H]$^-$. $^1$H NMR (CDCl3): 1.49 (d, J=6.96, 6H, CH$_3$); 3.49 (s, 3H, CH$_3$), 3.58 (sep, J=6.96, 1H, CH).

Example 4

3-Isopropyl-5-methylsulfonyl-7-[4-(2-pyridyl)benzyl]amino-1(2)H-pyrazolo[4,3-d]pyridine (8)

7-Chloro-3-isopropyl-5-methylsulfonyl-1(2)H-pyrazolo[4,3-d]pyridine (6) (4.89 g, 17.8 mmol) and ethyldiisopropylamine (4 mL, 22.5 mmol) were heated with stirring in 80 mL t-BuOH at 60° C. Solution of 1-[4-(pyridin-2-yl)phenyl] methanamine (3.84 g, 20.9 mmol) in 30 mL t-BuOH (50° C.) was added and the reaction mixture was heated at 60° C. for 1 h. The product started to crystallize after 10 min. After cooling to room temperature the product was filtered off, washed by MeOH and dried in vacuum, mp 213-216° C., yield 85%, (6.4 g).

ESI+ m/z 423.3 [M+H]$^+$, ESI− m/z 421.3 [M−H]$^-$. $^1$H (500 MHz; DMSO-d$_6$): 1.36 (d, J=7.03 Hz, 6H, —CH—(CH$_3$)$_2$); 2.43 (s, 3H, —CH3); 3.31-3.35 (m, 1H, —CH—(CH$_3$)$_2$); 4.75 (bs, 2H, —NH—CH$_2$—); 7.32 (ddd, J=7.34 Hz, J=4.89 Hz, J=0.92 Hz, 1H, ArH); 7.48 (d, J=7.03 Hz, 2H, ArH); 7.84 (dt, J=7.64 Hz, J=1.53 Hz, 1H, ArH); 7.92 (d, J=7.95 Hz, 1H, ArH); 8.05 (bd, J=7.03 Hz, 2H, ArH); 8.63 (bd, J=4.58 Hz, 1H, ArH).

Example 5

3-Isopropyl-5-(N-morpholinyl)-7-[4-(2-pyridyl)benzyl]amino-1(2)H-pyrazolo[4,3-d]pyridine (9)

Mixture of 3-isopropyl-5-methylsulfonyl-7-[4-(2-pyridyl)benzyl]amino-1(2)H-pyrazolo[4,3-d]pyridine (7) (0.36 g, 0.85 mmol) and morpholine (3 mL, 27 mmol) in sealed ampoule was heated at 150° C. for 8 h. Excess of morpholine was evaporated at temperature below 70° C. and the residue was partitioned between H$_2$O and CHCl$_3$. The combined organic phase was dried with sodium sulfate and evaporated under vacuum. The product was purified by column chromatography, stepwise 2%, 4%, 5% MeOH in CHCl$_3$. Chromatography afforded (after evaporation under vacuum) noncrystalizable amorphous colorless glass foam 0.15 g, yield 41%.

ESI+ m/z 430.1 [M+H]$^+$, ES− m/z 428.1 [M−H]$^-$. $^1$H (500 MHz; DMSO-d$_6$): 1.32 (d, J=7.03 Hz, 6H, —CH—(CH$_3$)$_2$); 3.18 (bs, 1H, —CH—(CH$_3$)$_2$); 3.58-3.60 (bs, 8H, 4x-CH$_2$—); 4.74 (bs, 2H, —NH—CH$_2$—); 7.31 (dd, J=6.72 Hz, J=5.50 Hz, 1H, ArH); 7.48 (d, J=7.95 Hz, 2H, ArH); 7.78 (bs, 1H, —NH—); 7.84 (dt, J=7.64 Hz, J=1.53 Hz, 1H, ArH); 7.91 (d, J=7.95 Hz, 1H, ArH); 8.04 (d, J=5.81 Hz, 2H, ArH); 8.63 (d, J=3.97 Hz, 1H, ArH); 11.84 (bs, 1H, —NH—).

Example 6

3-Isopropyl-5-(piperazin-1-yl)-7-[4-(2-pyridyl)benzyl]amino-1(2)H-pyrazolo[4,3-d]pyridine (13)

Solution of 3-isopropyl-5-methylsulfonyl-7-[4-(2-pyridyl)benzyl]amino-1(2)H-pyrazolo[4,3-d]pyridine (7) (0.32 g, 0.76 mmol) in pyrazine (3 mL, 27 mmol) in sealed ampoule was heated at 150° C. for 6 h. Excess of amine was evaporated at temperature below 70° C. and the residue was partitioned between H$_2$O and CHCl$_3$. The combined organic phase was dried with sodium sulfate and evaporated under vacuum. The product was purified by column chromatography, stepwise 2%, 4%, 5% MeOH in CHCl$_3$ with a trace of conc. aq. NH$_4$OH. Chromatography afforded (after evaporation under vacuum) noncrystalizable amorphous colorless glass foam 0.18 g, yield 55%.

ESI+ m/z 429.1 [M+H]$^+$, ES− m/z 427.1 [M−H]$^-$. $^1$H (500 MHz; DMSO-d$_6$): 1.31 (d, J=7.03 Hz, 6H, —CH—(CH$_3$)$_2$); 2.73-2.75 (m, 4H, 2x-CH$_2$—), 3.17 (sept., 1H, —CH—(CH$_3$)$_2$); 3.58-3.60 (m, 4H, 2x-CH$_2$—); 4.71 (d, J=5.20 Hz, 2H, —NH—CH$_2$—); 7.29 (ddd, J=7.34 Hz, J=4.89 Hz, J=0.92 Hz, 1H, ArH); 7.48 (d, J=8.25 Hz, 2H, ArH); 7.84 (dt, J=7.49 Hz, J=1.53 Hz, 1H, ArH); 7.91 (d, J=8.25 Hz, 1H, ArH); 8.04 (d, J=7.64 Hz, 2H, ArH); 8.63 (d, J=4.58 Hz, 1H, ArH).

Example 7

3-Isopropyl-5-(thiomorpholinyl)-7-[4-(2-pyridyl)benzyl]amino-1(2)H-pyrazolo[4,3-d]pyridine (15)

A mixture of 3-isopropyl-5-methylsulfonyl-7-[4-(2-pyridyl)benzyl]amino-1(2)H-pyrazolo[4,3-d]pyridine (7) (0.2 g, 0.47 mmol) and thiomorpholine (3 mL, 29 mmol) in sealed ampoule was heated at 150° C. for 5 h. Excess of thiomorpholine was evaporated at temperature below 70° C. and the residue was partitioned between H$_2$O and CHCl$_3$. The combined organic phase was dried with sodium sulfate and evaporated under vacuum. The product was purified by column chromatography, stepwise 2%, 3%, 4% MeOH in CHCl$_3$. Chromatography afforded (after evaporation under vacuum) noncrystallizable amorphous yellow glass foam 0.05 g, yield 24%.

ESI+ m/z 446.1 [M+H]$^+$, ES− m/z 444.1 [M−H]$^-$. $^1$H (500 MHz; CDCl3): 1.33 (d, J=6.72 Hz, 6H, —CH—(CH$_3$)$_2$); 2.55-2.57 (m, 4H, 2x-CH$_2$—); 3.30 (sept., J=6.72 Hz, 1H, —CH—(CH$_3$)$_2$); 4.07-4.09 (m, 4H, 2x-CH$_2$—); 4.64 (bd, J=5.20 Hz, 2H, —NH—CH$_2$—); 7.17-7.20 (m, 1H, ArH); 7.28 (d, J=8.25 Hz, 2H, ArH); 7.60 (d, J=7.95 Hz, 1H, ArH); 7.69 (dt, J=7.95 Hz, J=1.83 Hz, 1H, ArH); 7.79 (d, J=8.25 Hz, 2H, ArH); 8.60-8.62 (m, 1H, ArH).

Example 8

3-Isopropyl-5-[4-(2-hydroxyethyl)piperazin-1-yl]-7-[4-(2-pyridyl)benzyl]amino-1(2)H-pyrazolo[4,3-d]pyridine (17)

Solution of 3-isopropyl-5-methylsulfonyl-7-[4-(2-pyridyl)benzyl]amino-1(2)H-pyrazolo[4,3-d]pyridine (7) (0.21 g, 0.5 mmol) and 2-piperazin-1-ylethanol (3 mL, 23 mmol) in sealed ampoule was heated at 150° C. for 5 h. The reaction mixture was partitioned between H$_2$O and CHCl$_3$. The combined organic phase was dried with sodium sulfate and evaporated under vacuum. The product was purified by column chromatography, stepwise 2%, 3%, 4% MeOH in CHCl$_3$. Chromatography afforded a syrupy product which crystallizes from CHCl$_3$, mp 135-140° C., 0.035 g, yield 15%.

ESI+ m/z 473.1 [M+H]$^+$, ES− m/z 471.1 [M−H]$^-$. $^1$H (500 MHz; CDCl3+DMSO-d$_6$): 1.23 (d, J=7.03 Hz, 6H, —CH—(CH$_3$)$_2$); 2.45-2.46 (m, 6H, 3x-CH$_2$—); 3.14 (sept., J=6.72 Hz, 1H, —CH—(CH$_3$)$_2$); 3.50-3.52 (m, 2H, —CH$_2$—); 3.67 (m, 4H, 2x-CH$_2$—); 4.60-4.61 (m, 2H, —NH—CH$_2$—); 7.05-7.09 (m, 1H, ArH); 7.18 (bs, 1H, —NH—); 7.31-7.32 (m, 2H, ArH); 7.54-7.59 (m, 2H, ArH); 7.78-7.79 (m, 2H, ArH); 8.47-8.48 (m, 1H, ArH); 11.3 (bs, 1H, —NH—). $^{13}$C (125 MHz; CDCl3+DMSO-d$_6$): 21.6, 26.5, 44.0, 44.6, 52.9, 57.7, 59.8, 120.3, 122.2, 126.9, 128.4, 136.8, 138.3, 140.0, 149.6, 156.7, 157.9.

Example 9

3-Isopropyl-5(R)-(2-hydroxypropyl)amino-7-[4-(2-pyridyl)benzyl]amino-1(2)H-pyrazolo[4,3-d]pyridine (27)

Solution of 3-isopropyl-5-methylsulfonyl-7-[4-(2-pyridyl)benzyl]amino-1(2)H-pyrazolo[4,3-d]pyridine (7)

(1.25 g, 2.96 mmol) in R-(-)-1-amino-2-propanol (10 mL, 110 mmol) in sealed ampoule was heated at 150° C. for 3 h. Excess of amine was evaporated at temperature below 60° C. and the residue was partitioned between $H_2O$ and $CHCl_3$. The combined organic phase was dried with sodium sulfate and evaporated under vacuum. The product was purified by column chromatography, stepwise 3%, 5%, 7% MeOH in $CHCl_3$ with a trace of conc. aq. $NH_4OH$. Chromatography afforded (after evaporation under vacuum) noncrystallizable amorphous colorless glass form 0.65 g, yield 52%.

ESI+ m/z 418.1 (100%) [M+H]+, 209.6 (20%) [M+2H]2+, ESI- m/z 416.1 [M-H]-. 1H (500 MHz; DMSO-$d_6$+CDCl$_3$): 0.99 (d, J=6.42 Hz, 3H, —CH$_3$); 1.27 (d, J=7.03 Hz, 6H, —CH—(CH$_3$)$_2$); 3.06-3.11 (m, 2H, —CH$_2$—); 3.20-3.23 (m, 1H, —CH—(CH$_3$)$_2$); 3.72-3.75 (m, 1H, —CH—); 4.69 (bs, 2H, —NH—CH$_2$—); 6.02 (bs, 1H, —NH—CH$_2$—); 7.27-7.30 (m, 1H, ArH); 7.45 (d, J=7.34 Hz, 2H, ArH); 7.63 (bs, 1H, —NH—); 7.82 (dt, J=7.64 Hz, J=1.53 Hz, 1H, ArH); 7.88-7.89 (m, 1H, ArH); 8.01 (s, 2H, ArH); 8.60 (d, J=3.97 Hz, 1H, ArH); 11.76 (bs, 1H, —NH—). 13C (125 MHz; DMSO-$d_6$+CDCl$_3$): 21.9, 22.2, 26.6, 43.4, 49.9, 66.7, 120.5, 122.8, 127.2, 128.4, 137.7, 149.8, 156.3. αD23=+2.6° (MeOH, c=0,499 g/dl)

Example 10

3-Isopropyl-5-(2-hydroxy-2-methylpropyl)amino-7-[4-(2-pyridyl)benzyl]amino-1(2)H-pyrazolo[4,3-d]pyridine (33)

A mixture of 3-isopropyl-5-methylsulfonyl-7-[4-(2-pyridyl)benzyl]amino-1(2)H-pyrazolo[4,3-d]pyridine (7) (0.6 g, 1.42 mmol) and 1-amino-2-methyl-2-propanol (1.25 g, 14 mmol) was heated at 155° C. for 10 h in a sealed ampoule. After cooling the reaction mixture was partitioned between $H_2O$ and $CHCl_3$. The combined organic phase was dried with sodium sulfate and evaporated under vacuum. The product was purified by column chromatography, stepwise 3%, 5%, 7% MeOH in $CHCl_3$. Chromatography afforded (after evaporation under vacuum) noncrystalizable amorphous colorless glass form 0.2 g, yield 33%.

ESI+ m/z 432.1 [M+H]+, ES- m/z 430.1 [M-H]-. 1H (500 MHz; DMSO-$d_6$): 1.06 (s, 6H, —C—(CH$_3$)$_2$); 1.29 (d, J=7.03 Hz, 6H, —CH—(CH$_3$)$_2$); 3.14 (sept., J=7.03 Hz, 1H, —CH—(CH$_3$)$_2$); 3.20 (d, J=5.81 Hz, 2H, —NH—CH$_2$—); 4.73 (d, J=4.89 Hz, 2H, —NH—CH$_2$—); 6.12 (bs, 1H, —NH—CH$_2$—); 7.31 (dd, J=7.03 Hz, J=5.50 Hz, 1H, ArH); 7.48 (d, J=7.95 Hz, 2H, ArH); 7.84 (dt, J=7.64 Hz, J=1.53 Hz, 1H, ArH); 7.91 (d, J=7.95 Hz, 1H, ArH); 8.04 (d, J=7.64 Hz, 2H, ArH); 8.63 (d, J=4.28 Hz, 1H, ArH).

Example 11

3-Isopropyl-5-(3-amino-2-hydroxypropyl)amino-7-[4-(2-pyridyl)benzyl]amino-1(2)H-pyrazolo[4,3-d]pyridine (45)

A mixture of 3-isopropyl-5-methylsulfonyl-7-[4-(2-pyridyl)benzylamino]-1(2)H-pyrazolo[4,3-d]pyridine (7) (0.69 g, 1.64 mmol), 1,3-diamino-2-propanol (10 mL, 95 mmol) and 1-methyl-2-pyrolidone 2 mL was heated at 150° C. for 6 h in a sealed ampoule. Excess of amine was evaporated at temperature below 70° C. and the residue was partitioned between $H_2O$ and $CHCl_3$. The combined organic phase was dried with sodium sulfate and evaporated under vacuum. The product was purified by column chromatography, stepwise 5%, 8%, 11% 14% MeOH in $CHCl_3$ with a trace of conc. aq. $NH_4OH$. Chromatography afforded (after evaporation under vacuum) noncrystalizable amorphous colorless glass form 0.17 g, yield 24%.

ESI+ m/z 433.1 (100%) [M+H]+, 217.6 (90%) [M+2H]2+, ESI- m/z 431.1 [M-H]-. 1H (500 MHz; DMSO-$d_6$): 1.27 (d, J=7.03 Hz, 6H, —CH—(CH$_3$)$_2$); 2.40-2.50 (m, 2H, —CH$_2$—); 3.10-3.20 (m, 2H, —CH$_2$—); 2.28-2.33 (m, 1H, —CH—); 3.45-3.49 (m, 1H, —CH—(CH$_3$)$_2$); 4.69 (bs, 2H, —NH—CH$_2$—); 6.06 (app. bt, 1H, —NH—CH$_2$—); 7.26-7.29 (m, 1H, ArH); 7.44 (d, J=8.25 Hz, 2H, ArH); 7.81 (dt, J=7.64 Hz, J=1.83 Hz, 1H, ArH); 7.87-7.89 (m, 2H, ArH, —NH—); 8.01 (d, J=8.56 Hz, 2H, ArH); 8.59-8.60 (m, 1H). 13C (125 MHz; DMSO-$d_6$): 22.1, 22.2, 26.2, 43.1, 45.7, 46.0, 72.8, 120.6, 123.0, 126.7, 127.0, 127.8, 128.4, 137.7, 137.9, 140.9, 150.0, 156.3, 158.9.

Example 12

3-Isopropyl-5-[2-(dimethylamino)ethyl]amino-7-[4-(2-pyridyl)benzyl]amino-1(2)H-pyrazolo[4,3-d]pyridine (47)

Solution of 3-isopropyl-5-methylsulfonyl-7-[4-(2-pyridyl)benzyl]amino-1(2)H-pyrazolo[4,3-d]pyridine (7) (0.3 g, 0.71 mmol) and 2-(dimethylamino)ethylamine (3 mL, 27 mmol) in sealed ampoule was heated at 150° C. for 1 h. Excess of amine was evaporated at temperature below 50° C. and the residue was partitioned between $H_2O$ and $CHCl_3$. The combined organic phase was dried with sodium sulfate and evaporated under vacuum. The product was purified by column chromatography, stepwise 5%, 10%, 14% MeOH in $CHCl_3$ with a trace of conc. aq. $NH_4OH$. Chromatography afforded noncrystalizable amorphous colorless glass foam, 0.06 g, yield 20%.

ESI+ m/z m/z 431.2 (100%) [M+H]+, 216.1 (30%) [M+2H]2+, ESI- m/z 429.2 [M-H]-. 1H (500 MHz; CDCl$_3$): 1.31 (d, J=7.03 Hz, 6H, —CH—(CH$_3$)$_2$); 2.23 (s, 6H, 2x-CH$_3$); 2.65 (t, J=7.64 Hz, 2H, —CH$_2$—); 3.20 (t, J=7.34, 2H, —CH$_2$—); 3.27 (kvint.; J=7.03 Hz, 1H, —CH—(CH$_3$)$_2$); 4.61 (bs, 2H, —NH—CH$_2$—); 6.97 (bs, 1H, —NH—CH—); 7.14-7.18 (m, 3H, ArH); 7.55 (d, J=8.25 Hz, 1H, ArH); 7.66 (dd, J=7.64 Hz, J=1.83 Hz, 1H, ArH); 7.69 (d, J=7.95 Hz, 2H, ArH); 8.55 (d, J=3.97 Hz, 1H, ArH). 13C (125 MHz; CDCl3): 21.8; 26.4; 28.1; 44.0; 45.1; 59.1; 120.9; 122.3; 127.1; 128.0; 137.2; 138.2; 139.1; 149.4; 150.7; 157.0; 161.7.

Example 13

3-Isopropyl-5-(trans-2-aminocyclohexyl)amino-7-[4-(2-pyridyl)benzyl]amino-1(2)H-pyrazolo[4,3-d]pyridine (64)

Solution of 3-isopropyl-5-methylsulfonyl-7-[4-(2-pyridyl)benzyl]amino-1(2)H-pyrazolo[4,3-d]pyridine (7) (1.4 g, 3.32 mmol) in 1,2-trans-diaminocyclohexane (30 mL, 68 mmol) in sealed ampoule was heated at 155° C. for 20 h. Excess of amine was evaporated at temperature below 70° C. and the residue was partitioned between $H_2O$ and $CHCl_3$. The combined organic phase was dried with sodium sulfate and evaporated under vacuum. The product was purified by column chromatography, stepwise 4%, 8%, 11%, 14% MeOH in $CHCl_3$ with a trace of conc. aq. $NH_4OH$. Chromatography afforded (after evaporation under vacuum) noncrystalizable amorphous colorless glass foam 0.20 g, yield 13%.

ESI+ m/z 457.3 (100%) [M+H]$^+$, 229.1 (50%) [M+2H]$^{2+}$, ESI– m/z 455.3 [M–H]$^-$. $^1$H (500 MHz; CDCl$_3$): 1.13-1.20 (m, 4H, —CH$_2$—); 1.25 (bs, 6H, —CH—(CH$_3$)$_2$); 1.57-1.59 (m, 2H, —CH$_2$—); 1.86 (bs, 2H, —CH$_2$—); 2.47 (bs, 1H, —CH—); 3.15 (sept., J=6.42 Hz, 1H, —CH—(CH$_3$)$_2$); 3.56 (bs, 1H, —CH—); 4.57 (bs, 2H, —NH—CH$_2$—); 7.13 (dd, J=7.34 Hz, J=4.89 Hz, 1H, ArH); 7.28 (d, J=7.95 Hz, 2H, Ar); 7.53 (d, J=7.95 Hz, 1H, ArH); 7.63 (d, J=7.64 Hz, 1H, ArH); 7.73 (d, J=7.95 Hz, 2H, ArH); 8.58 (d, J=4.58 Hz, 1H, ArH). $^{13}$C (125 MHz; CDCl$_3$): 18.3; 21.7; 21.8; 24.7; 25.0; 25.9; 32.5; 34.0; 43.7; 46.0; 56.3; 57.2; 57.9; 120.4; 121.9; 126.8; 127.0; 127.4; 127.7; 136.7; 137.9; 139.6; 149.3; 149.6; 151.8; 156.9; 158.0.

Example 14

3-Isopropyl-5-(trans-4-aminocyclohexyl)amino-7-[4-(2-pyridyl)benzyl]amino-1(2)H-pyrazolo[4,3-d]pyridine (67)

3-Isopropyl-5-methylsulfonyl-7-[4-(2-pyridyl)benzyl]amino-1(2)H-pyrazolo[4,3-d]pyridine (7) (0.3 g, 0.71 mmol) in melted 1,4-trans-diaminocyclohexane (5 g, 44 mmol) in sealed ampoule was heated at 150° C. for 20 h. Excess of amine was evaporated at temperature below 70° C. and the residue was partitioned between H$_2$O and CHCl$_3$. The combined organic phase was dried with sodium sulfate and evaporated under vacuum. The product was purified by column chromatography, stepwise 4%, 8%, 11%, 14% MeOH in CHCl$_3$ with a trace of conc. aq. NH$_4$OH. Chromatography afforded (after evaporation under vacuum) noncrystalizable amorphous colorless glass foam 0.06 g, yield 19%.

ESI+ m/z 457.3 (100%) [M+H]$^+$, 229.1 (50%) [M+2H]$^{2+}$, ESI– m/z 455.3 [M–H]$^-$. $^1$H (500 MHz; DMSO-d$_6$): 1.08-1.18 (m, 4H, 2x-CH$_2$—); 1.27 (d, J=7.03 Hz, 6H, —CH—(CH$_3$)$_2$); 1.71-1.72 (m, 2H, —CH$_2$—); 1.85-1.87 (m, 2H, —CH$_2$—); 2.50-2.52 (m, 1H, —CH—NH—); 3.11 (sept., J=7.03 Hz, 1H, —CH—(CH$_3$)$_2$); 3.54-3.56 (m, 1H, —CH—NH—); 4.68 (bd, J=4.58 Hz, 2H, —NH—CH$_2$—); 5.69 (bd, J=7.34 Hz, 1H, —NH—CH—); 7.26 (m, 1H, ArH); 7.44 (d, J=8.25 Hz, 2H, ArH); 7.79-7.82 (m, 2H, ArH, —NH—); 7.86-7.88 (m, 1H, ArH); 8.00 (d, J=8.25 Hz, 2H, ArH); 8.59-8.60 (m, 1H, ArH). $^{13}$C (125 MHz; DMSO-d6): 22.1; 26.4, 31.8, 34.9, 43.2, 50.0, 50.4, 120.6, 122.9, 127.0, 128.3, 137.7, 137.8, 141.2, 150.0, 156.3, 157.8.

Example 15

3-Isopropyl-5-(4-methoxybenzyl)amino-7-[4-(2-pyridyl)benzyl]amino-1(2)H-pyrazolo[4,3-d]pyridine (73)

Solution of 3-isopropyl-5-methylsulfonyl-7-[4-(2-pyridyl)benzyl]amino-1(2)H-pyrazolo[4,3-d]pyridine (7) (0.5 g, 1.18 mmol) in 4-methoxybenzylamine (10 mL, 58 mmol) in sealed ampoule was heated at 155° C. for 5 h. Excess of amine was evaporated at temperature below 70° C. and the residue was partitioned between H$_2$O and CHCl$_3$. The combined organic phase was dried with sodium sulfate and evaporated under vacuum. The product was purified by column chromatography, stepwise 3%, 5%, 7% MeOH in CHCl$_3$. Chromatography afforded (after evaporation under vacuum) noncrystalizable amorphous colorless glass foam 0.15 g, yield 26%.

ESI+ m/z 480.3 [M+H]$^+$, ES– m/z 478.3 [M–H]$^-$. $^1$H (500 MHz; CDCl3): 1.29 (d, J=6.72 Hz, 6H, —CH—(CH$_3$)$_2$); 3.21 (sept., J=6.72 Hz, 1H, —CH—(CH$_3$)$_2$); 3.67 (s, 3H, —CH$_3$); 4.50 (bd, J=3.97 Hz, 2H, —NH—CH$_2$—); 4.69 (bs, 2H, —NH—CH$_2$—); 6.72 (d, J=8.56 Hz, 2H, ArH); 7.17-7.22 (m, 3H, ArH, —NH—); 7.29 (d, J=8.25 Hz, 2H, ArH); 7.59 (d, J=7.95 Hz, 1H, ArH); 7.69 (dt, J=7.64 Hz, J=1.83 Hz, 1H, ArH); 7.78 (d, J=8.25 Hz, 2H, ArH); 8.60-8.61 (m, 1H, ArH). $^{13}$C (125 MHz; CDCl3): 21.8, 26.1, 44.2, 45.4, 55.3, 113.8, 120.7, 122.3, 127.1, 128.1, 128.4, 128.9, 129.0, 137.4, 138.4, 149.6, 157.0, 158.7.

Example 16

3-Isopropyl-5(R)-[1-(hydroxymethyl)propyl]amino-7-[4-(2-pyridyl)benzyl]amino-1(2)H-pyrazolo[4,3-d]pyridine (83)

Solution of 3-Isopropyl-5-methylsulfonyl-7-[4-(2-pyridyl)benzyl]amino-1(2)H-pyrazolo[4,3-d]pyridine (7) (0.5 g, 1.19 mmol) in R-(–)-2-amino-1-butanol (5 mL, 50 mmol) was heated at 154° C. for 8 h in a sealed ampoule. Excess of amine was evaporated at temperature below 70° C. and the residue was partitioned between H$_2$O and CHCl$_3$. The combined organic phase was dried with sodium sulfate and evaporated under vacuum. The product was purified by column chromatography, stepwise 3%, 5%, 7% MeOH in CHCl$_3$ with a trace of conc. aq. NH$_4$OH. Chromatography afforded (after evaporation under vacuum) noncrystalizable amorphous colorless glass form 0.14 g, yield 27%.

ESI+ m/z 432.1 [M+H]$^+$, ESI– m/z 430.1 [M–H]$^-$. $^1$H (500 MHz; DMSO-d$_6$): 0.81 (t, J=6.72 Hz, 3H, —CH$_2$—CH$_3$); 1.39-1.45 (m, 7H, —CH(CH$_3$)$_2$, —CHα-CH$_3$); 1.55-1.59 (m, 1H, —CHβ-CH$_3$); 3.43-3.47 (m, 1H, —CH(CH$_3$)$_2$); 3.77-3.80 (m, 1H, —CH—NH—); 4.49-4.67 (m, 4H, —CH$_2$—OH, —NH—CH$_2$—); 5.82 (d, J=7.64 Hz, 1H, —NH—CH$_2$—); 7.29-7.31 (m, 1H, ArH); 7.44 (d, J=7.95 Hz, 2H, ArH); 7.78 (s, 1H); 7.83 (t, J=8.01 Hz, 1H, ArH); 7.89 (d, J=7.95 Hz, 1H, ArH); 7.99 (d, J=8.25 Hz, 2H, ArH); 8.62 (bd, J=4.58 Hz, 1H, ArH. αD23=+45.50 (MeOH, c=0,191 g/dl).

TABLE 1

Compounds Prepared by the Method of Examples 1-16.

| No | SUBSTITUENT R | CHN ANALYSES [%] | MS (ZMD)- ANALYSES | |
|---|---|---|---|---|
| | | | [M – H]$^-$ a) | [M + H]$^+$ b) |
| 9 | N-morfolinyl | C = 64.11; H = 6.34; N = 22.83 | 428.2 | 430.2 |
| 10 | N-pyrrolidinyl | C = 69.70; H = 6.59; N = 23.70 | 412.2 | 414.2 |
| 11 | N-pyrazolidinyl | C = 66.64; H = 6.31; N = 27.02 | 413.2 | 415.2 |
| 12 | N-imidazolidinyl | C = 66.63; H = 6.32; N = 27.03 | 413.2 | 415.1 |
| 13 | N-piperazinyl | C = 67.27; H = 6.59; N = 26.15 | 427.2 | 429.2 |
| 14 | N-piperidinyl | C = 70.23; H = 6.84; N = 22.93 | 426.3 | 428.2 |
| 15 | N-thiomorfolinyl | C = 64.69; H = 6.11; N = 22.00 | 444.2 | 446.2 |

TABLE 1-continued

Compounds Prepared by the Method of Examples 1-16.

| No | SUBSTITUENT R | CHN ANALYSES [%] | MS (ZMD)- ANALYSES | |
|---|---|---|---|---|
| | | | $[M-H]^-$ a) | $[M+H]^+$ b) |
| 16 | 4-methylpiperazin-1-yl | C = 67.85; H = 6.82; N = 25.32 | 441.3 | 443.2 |
| 17 | 4-(2-hydroxyethyl)piperazin-1-yl | C = 66.08; H = 6.83; N = 23.71 | 471.3 | 473.2 |
| 18 | ethylamino | C = 68.19; H = 6.50; N = 25.30 | 386.2 | 388.2 |
| 19 | propylamino | C = 68.80; H = 6.77; N = 24.41 | 400.2 | 402.2 |
| 20 | butylamino | C = 69.38; H = 7.03; N = 23.60 | 414.2 | 416.2 |
| 21 | pentylamino | C = 69.90; H = 7.27; N = 22.82 | 428.2 | 430.2 |
| 22 | hexylamino | C = 70.41; H = 7.50; N = 22.10 | 442.3 | 444.2 |
| 23 | heptylamino | C = 70.87; H = 7.71; N = 21.42 | 456.3 | 458.3 |
| 24 | octylamino | C = 71.30; H = 7.90; N = 20.79 | 470.3 | 472.3 |
| 25 | (2-hydroxyethyl)amino | C = 65.49; H = 6.25; N = 24.30 | 402.2 | 404.2 |
| 26 | (R/S)-(2-hydroxypropyl)amino | C = 66.17; H = 6.52; N = 23.48 | 416.2 | 418.2 |
| 27 | (R)-(2-hydroxypropyl)amino | C = 66.18; H = 6.52; N = 23.48 | 416.2 | 418.2 |
| 28 | (S)-(2-hydroxypropyl)amino | C = 66.17; H = 6.53; N = 23.48 | 416.2 | 418.2 |
| 29 | (3-hydroxypropyl)amino | C = 66.17; H = 6.52; N = 23.47 | 416.2 | 418.2 |
| 30 | (R/S)-(4-hydroxybut-2-yl)amino | C = 66.80; H = 6.77; N = 22.72 | 430.2 | 432.2 |
| 31 | (R)-(4-hydroxybut-2-yl)amino | C = 66.80; H = 6.78; N = 22.72 | 430.2 | 432.2 |
| 32 | (S)-(4-hydroxybut-2-yl)amino | C = 66.81; H = 6.77; N = 22.72 | 430.2 | 432.2 |
| 33 | (2-hydroxy-2-methylpropyl)amino | C = 66.80; H = 6.77; N = 22.72 | 430.2 | 432.2 |
| 34 | (3-hydroxy-3-methylbutyl)amino | C = 67.39; H = 7.01; N = 22.01 | 444.2 | 446.2 |
| 35 | (2,3-dihydroxypropyl)amino | C = 63.72; H = 6.28; N = 22.62 | 432.2 | 434.2 |
| 36 | (1-hydroxy-3-methylbut-2-yl)amino | C = 67.39; H = 7.01; N = 22.01 | 444.3 | 446.2 |
| 37 | (R/S)-(2-hydroxypent-3-yl)amino | C = 67.39; H = 7.01; N = 22.01 | 444.2 | 446.2 |
| 38 | (R)-(2-hydroxypent-3-yl)amino | C = 67.39; H = 7.02; N = 22.01 | 444.2 | 446.2 |
| 39 | (S)-(2-hydroxypent-3-yl)amino | C = 67.39; H = 7.01; N = 22.02 | 444.2 | 446.2 |
| 40 | (2-aminoethyl)amino | C = 65.65; H = 6.51; N = 27.84 | 401.2 | 403.2 |
| 41 | (3-aminopropyl)amino | C = 66.32; H = 6.78; N = 26.90 | 415.2 | 417.2 |
| 42 | (4-aminobutyl)amino | C = 66.95; H = 7.02; N = 26.03 | 429.3 | 431.2 |
| 43 | (5-aminopentyl)amino | C = 67.54; H = 7.26; N = 25.20 | 443.3 | 445.2 |
| 44 | (6-aminohexyl)amino | C = 68.10; H = 7.47; N = 24.43 | 457.3 | 459.3 |
| 45 | (3-amino-2-hydroxypropyl)amino | C = 63.87; H = 6.53; N = 25.91 | 431.2 | 433.2 |
| 46 | [1-(dimethylamino)methyl]amino | C = 66.32; H = 6.78; N = 26.90 | 415.2 | 417.2 |
| 47 | [2-(dimethylamino)ethyl]amino | C = 66.95; H = 7.02; N = 26.03 | 429.2 | 431.2 |
| 48 | [3-(dimethylamino)propyl]amino | C = 67.54; H = 7.26; N = 25.20 | 443.3 | 445.3 |
| 49 | [4-(dimethylamino)butyl]amino | C = 68.09; H = 7.47; N = 24.43 | 457.3 | 459.3 |
| 50 | [2-(diethylamino)ethyl]amino | C = 68.09; H = 7.47; N = 24.43 | 457.3 | 459.3 |
| 51 | [3-(diethylamino)propyl]amino | C = 68.61; H = 7.68; N = 23.71 | 471.3 | 473.3 |
| 52 | [3-(diethylamino)butyl]amino | C = 69.10; H = 7.87; N = 23.03 | 485.3 | 487.3 |
| 53 | 2-(aziridin-1-yl)ethylamino | C = 67.27; H = 6.59; N = 26.15 | 427.2 | 429.2 |
| 54 | 2-(azetidin-1-yl)ethylamino | C = 67.85; H = 6.83; N = 25.32 | 441.3 | 443.3 |
| 55 | 2-(azolidin-1-yl)ethylamino | C = 68.39; H = 7.06; N = 24.54 | 455.3 | 457.3 |
| 56 | 2-(piperidin-1-yl)ethylamino | C = 68.91; H = 7.28; N = 23.81 | 469.3 | 471.3 |
| 57 | 2-(aziridin-1-yl)propylamino | C = 67.85; H = 6.83; N = 25.32 | 441.2 | 443.2 |
| 58 | 2-(azetidin-1-yl)propylamino | C = 68.39; H = 7.06; N = 24.54 | 455.3 | 457.3 |
| 59 | cyclopropylamino | C = 69.15; H = 6.31; N = 24.54 | 398.2 | 400.2 |
| 60 | cyclobutylamino | C = 69.71; H = 6.58; N = 23.71 | 412.2 | 414.2 |
| 61 | cyclopentylamino | C = 70.23; H = 6.84; N = 22.93 | 426.2 | 428.2 |
| 62 | cyclohexylamino | C = 70.72; H = 7.08; N = 22.20 | 440.3 | 442.3 |
| 63 | cis-(2-aminocyclohexyl)amino | C = 68.39; H = 7.06; N = 24.54 | 455.3 | 457.2 |
| 64 | trans-(2-aminocyclohexyl)amino | C = 68.39; H = 7.05; N = 24.54 | 455.3 | 457.2 |
| 65 | cis,trans-(2-aminocyclohexyl)amino | C = 68.39; H = 7.06; N = 24.53 | 455.3 | 457.2 |
| 66 | cis,trans-(3-aminocyclohexyl)amino | C = 68.40; H = 7.06; N = 24.54 | 455.3 | 457.2 |
| 67 | trans-(4-aminocyclohexyl)amino | C = 68.39; H = 7.06; N = 24.54 | 455.3 | 457.2 |
| 68 | trans-(2-hydroxycyclohexyl)amino | C = 68.25; H = 6.83; N = 21.43 | 456.2 | 458.2 |
| 69 | trans-(3-hydroxycyclohexyl)amino | C = 68.25; H = 6.83; N = 21.44 | 456.2 | 458.2 |
| 70 | trans-(4-hydroxycyclohexyl)amino | C = 68.24; H = 6.83; N = 21.43 | 456.2 | 458.2 |
| 71 | (2-methoxybenzyl)amino | C = 70.12; H = 6.10; N = 20.44 | 478.2 | 480.2 |
| 72 | (3-methoxybenzyl)amino | C = 70.13; H = 6.09; N = 20.44 | 478.2 | 480.2 |
| 73 | (4-methoxybenzyl)amino | C = 70.12; H = 6.10; N = 20.45 | 478.2 | 480.2 |
| 74 | 3,5-dimethoxybenzylamino | C = 68.35; H = 6.13; N = 19.24 | 508.2 | 510.2 |
| 75 | 2,6-dimethoxybenzylamino | C = 68.35; H = 6.13; N = 19.24 | 508.2 | 510.2 |
| 76 | 2,4,6-trimethoxybenzylamino | C = 66.77; H = 6.16; N = 18.17 | 538.2 | 540.2 |
| 77 | 3,4,5-trimethoxybenzylamino | C = 66.77; H = 6.16; N = 18.17 | 538.2 | 540.2 |
| 78 | 2-fluorobenzylamino | C = 69.36; H = 5.61; N = 20.97 | 466.2 | 468.2 |
| 79 | 3-fluorobenzylamino | C = 69.36; H = 5.61; N = 20.97 | 466.2 | 468.2 |
| 80 | 4-fluorobenzylamino | C = 69.36; H = 5.61; N = 20.97 | 466.2 | 468.2 |
| 81 | 2-chlorobenzylamino | C = 67.00; H = 5.41; N = 20.26 | 482.2 | 484.2 |
| 82 | 3-chlorobenzylamino | C = 67.00; H = 5.41; N = 20.26 | 482.2 | 484.2 |
| 82 | 4-chlorobenzylamino | C = 67.00; H = 5.41; N = 20.26 | 482.2 | 484.2 |
| 83 | (R)-[1-(hydroxymethyl)propyl]amino | C = 66.80; H = 6.77; N = 22.72 | 430.2 | 432.2 |
| 84 | (S)-[1-(hydroxymethyl)propyl]amino | C = 66.80 H = 6.77; N = 22.71 | 430.2 | 432.2 | a) solution: MeOH p.a. + HCOOH
b) solution: MeOH p.a. + $H_2O$ + $NH_3$

Example 17

Antileukemic Activity of Novel Compounds In Vitro

Cytotoxicity of the compounds is the major property determining their antileukemic efficacy in vivo. One of the parameters used, as the basis for cytotoxicity assays, is the metabolic activity of viable cells. For example, a microtiter assay, which uses (3-(4,5-dimethylthiazol-2-yl)-2,5-diphenyltetrazolium bromide (MTT), is widely used to quantitate cell proliferation and cytotoxicity. This assay is widely used in drug screening programs and in chemosensitivity testing. Because only metabolically active living cells reduce MTT to correspond purple formazan dye, these assays detect viable cells exclusively. The quantity of reduced MTT corresponds to the number of vital cells in the culture.

The compounds were assayed using the following leukemic cell lines: K562 (human chronic myelogenous leukaemia), HL60 (human promyelocytic leukaemia), CEM (human lymphoblastoid leukaemia), THP1 (human monocytic cell line), MV4; 11 (acute myelocytic leukemia). All cell lines were grown in RPMI medium supplemented with fetal bovine serum and L-glutamine and maintained at 37° C. in a humidified atmosphere with 5% $CO_2$. For cytotoxicity assays, 2000-5000 cells were seeded into each well of 96 well plate, allowed to stabilize for at least 8 h and then tested compounds were added at various concentrations ranging from 100 to 0.01 µM in triplicates. After three days, MTT solution (5 mg/ml; Sigma, St. Louis, USA) was added to cells and medium was replaced with DMSO after five hours. The absorbance was measured at 620 nm by employing a microplate reader. MTT assays were repeated 3 times for each drug application and untreated cells were used as reference. The $GI_{50}$ values, drug concentrations lethal to 50% of the cells, were calculated from the obtained dose response curves.

Significant activities were found in all five leukemic cell lines tested derived from patients diagnosed with various leukemias (for example results see Table 2). In general, the results indicate that they the novel derivatives are active in a broad range of various leukemic cells independently on their genetic background.

TABLE 2

In vitro antileukemic activity of novel compounds.

| Compound | $IC_{50}$ (µM) | | | | |
|---|---|---|---|---|---|
| | K562 | HL60 | CEM | THP1 | MV4;11 |
| 2 | 1.00 | 0.92 | 0.80 | 0.56 | 0.47 |
| 5 | 0.78 | 0.86 | 0.94 | 0.32 | 0.60 |
| 7 | 0.64 | 0.52 | 0.93 | 1.64 | 1.69 |
| 9 | 0.11 | 0.10 | 0.07 | 0.18 | 0.36 |
| 13 | 0.02 | 0.02 | 0.01 | 0.03 | 0.04 |
| 15 | 0.59 | 0.60 | 0.23 | 0.31 | 0.87 |
| 17 | 0.15 | 0.26 | 0.11 | 0.30 | 0.37 |
| 27 | 0.06 | 0.02 | 0.01 | 0.03 | 0.06 |
| 29 | 0.10 | 0.18 | 0.09 | 0.14 | 0.27 |
| 31 | 0.39 | 0.24 | 0.21 | 0.26 | 0.31 |
| 33 | 0.03 | 0.02 | 0.01 | 0.01 | 0.07 |
| 35 | 0.24 | 0.17 | 0.18 | 0.26 | 0.20 |
| 40 | 0.34 | 0.22 | 0.14 | 0.11 | 0.25 |
| 41 | 0.47 | 0.56 | 0.43 | 0.27 | 0.35 |
| 45 | 0.70 | 0.62 | 0.54 | 0.49 | 0.51 |
| 47 | 0.13 | 0.09 | 0.07 | 0.06 | 0.12 |
| 50 | 0.18 | 0.14 | 0.11 | 0.08 | 0.17 |
| 54 | 0.36 | 0.29 | 0.24 | 0.37 | 0.24 |
| 57 | 0.44 | 0.32 | 0.27 | 0.29 | 0.53 |
| 64 | 0.10 | 0.09 | 0.05 | 0.04 | 0.09 |
| 65 | 0.30 | 0.22 | 0.14 | 0.11 | 0.38 |
| 67 | 0.59 | 0.24 | 0.23 | 0.30 | 0.19 |
| 73 | 3.95 | 0.78 | 0.89 | 0.67 | 0.97 |
| 83 | 0.07 | 0.02 | 0.06 | 0.01 | 0.07 |

Example 18

Activity Against Cell Lines Derived from Solid Cancers

The compounds were assayed using the following cell lines: G361 (malignant melanoma), MCF7 (breast adenocarcinoma), PLC/PRF/5 (liver hepatoma), PANC-1 (pancreatic carcinoma) and HCT116 (colon carcinoma). All cell lines were grown in DMEM medium supplemented with fetal bovine serum and L-glutamine and maintained at 37° C. in a humidified atmosphere with 5% $CO_2$. For cytotoxicity assays, 4000-10000 cells were seeded into each well of a 96 well plate, allowed to stabilize for at least 16 h and then tested compounds were added at various concentrations ranging from 100 to 0.01 µM in triplicates. After three days, MTT solution (5 mg/ml; Sigma, St. Louis, USA) was added to cells and medium was replaced with DMSO after five hours. The absorbance was measured at 620 nm by employing a microplate reader. MTT assays were repeated 3 times for each drug application and untreated cells were used as reference. The $GI_{50}$ values, drug concentrations lethal to 50% of the cells, were calculated from the obtained dose response curves.

Significant activities were found in all five used cell lines derived from solid cancers with various histopathological origins and exhibiting various molecular alterations (Table 3).

TABLE 3

In vitro activity against cell lines derived from solid cancers.

| Compound | $IC_{50}$ (µM) | | | | |
|---|---|---|---|---|---|
| | G361 | MCF7 | PLC/PRF/5 | PANC-1 | HCT116 |
| 2 | 0.78 | 1.19 | 0.97 | 0.46 | 1.20 |
| 5 | 0.24 | 0.81 | 0.70 | 0.65 | 1.30 |
| 7 | 0.43 | 0.46 | 0.21 | 1.56 | 1.97 |
| 9 | 0.25 | 0.16 | 0.21 | 0.30 | 0.42 |
| 13 | 0.02 | 0.02 | 0.05 | 0.06 | 0.03 |
| 15 | 0.42 | 0.53 | 0.20 | 0.34 | 0.69 |
| 17 | 0.24 | 0.19 | 0.73 | 0.34 | 0.40 |
| 27 | 0.08 | 0.03 | 0.04 | 0.07 | 0.10 |
| 33 | 0.03 | 0.02 | 0.05 | 0.01 | 0.04 |
| 45 | 0.22 | 0.31 | 0.20 | 0.32 | 0.37 |
| 47 | 0.47 | 0.23 | 0.24 | 0.20 | 0.34 |
| 64 | 0.15 | 0.22 | 0.14 | 0.08 | 0.34 |
| 65 | 0.04 | 0.06 | 0.05 | 0.02 | 0.08 |
| 67 | 0.36 | 0.47 | 0.29 | 0.50 | 0.37 |
| 73 | 2.62 | 5.30 | 3.94 | 0.44 | 0.99 |
| 83 | 0.04 | 0.05 | 0.02 | 0.02 | 0.03 |

Example 19

CDK Inhibition

CDK2/Cyclin E kinase was produced in Sf9 insect cells via baculoviral infection and purified on a NiNTA column (Qiagen). The kinase reactions were assayed with 1 mg/mL histone H1 in the presence of 15 μM ATP, 0.05 μCi [γ-$^{33}$P] ATP and of the test compound in a final volume of 10 μL, all in a reaction buffer (60 mM HEPES-NaOH, pH 7.5, 3 mM MgCl$_2$, 3 mM MnCl$_2$, 3 μM Na-orthovanadate, 1.2 mM DTT, 2.5 μg/50 μl PEG$_{20.000}$). CDK5/p35 was purchased from ProQinase GmbH. The kinase reactions were assayed with 1 mg/mL histone H1 in the presence of 0.15 μM ATP, 0.05 μCi [γ-$^{33}$P]ATP and of the test compound in a final volume of 10 μL, all in a reaction buffer (60 mM HEPES-NaOH, pH 7.5, 3 mM MgCl$_2$, 3 mM MnCl2, 3 μM Na-orthovanadate, 1.2 mM DTT, 2.5 μg/50 μl PEG$_{20.000}$).

The reactions were stopped by adding 5 μL of 3% aq H$_3$PO$_4$. Aliquots were spotted onto P-81 phosphocellulose (Whatman), washed 3× with 0.5% aq H$_3$PO$_4$ and finally air-dried. Kinase inhibition was quantified using digital image analyzer FLA-7000 (GE Healthcare Life Sciences) and expressed as a residual activity of kinase or as IC$_{50}$, the concentration of the test compounds required to decrease the CDK by 50%.

As shown in Table 4, all compounds potently inhibited CDK2 and CDK5 in a nanomolar range. Inhibition of CDK2 leads to block of cell cycle preferentially in G1/S transition and during S phase, when DNA is replicated. As a result, the proliferation of cancer cells is inhibited.

TABLE 4

Kinase inhibitory activity of selected compounds expressed as IC$_{50}$.

| Compound | IC$_{50}$ (μM) | |
| --- | --- | --- |
| | CDK2 | CDK5 |
| 2 | 0.197 | 0.183 |
| 5 | 0.048 | 0.229 |
| 7 | 0.070 | 0.165 |
| 9 | 0.018 | 0.005 |
| 13 | 0.050 | 0.119 |
| 14 | 0.042 | 0.180 |
| 15 | 0.061 | 0.114 |
| 17 | 0.132 | 0.422 |
| 27 | 0.021 | 0.005 |
| 29 | 0.039 | 0.0149 |
| 33 | 0.009 | 0.001 |
| 35 | 0.012 | 0.017 |
| 40 | 0.027 | 0.038 |
| 45 | 0.051 | 0.017 |
| 47 | 0.467 | 2.136 |
| 54 | 0.322 | 0.204 |
| 55 | 0.640 | 0.182 |
| 64 | 0.046 | 0.088 |
| 65 | 0.023 | 0.048 |
| 67 | 0.096 | 0.179 |
| 73 | 1.483 | 4.415 |
| 83 | 0.054 | 0.009 |
| 84 | 0.098 | 0.021 |

Example 20

Novel Compounds Alter Cell Cycle Profile in Treated Cancer Cells

Figure 1:
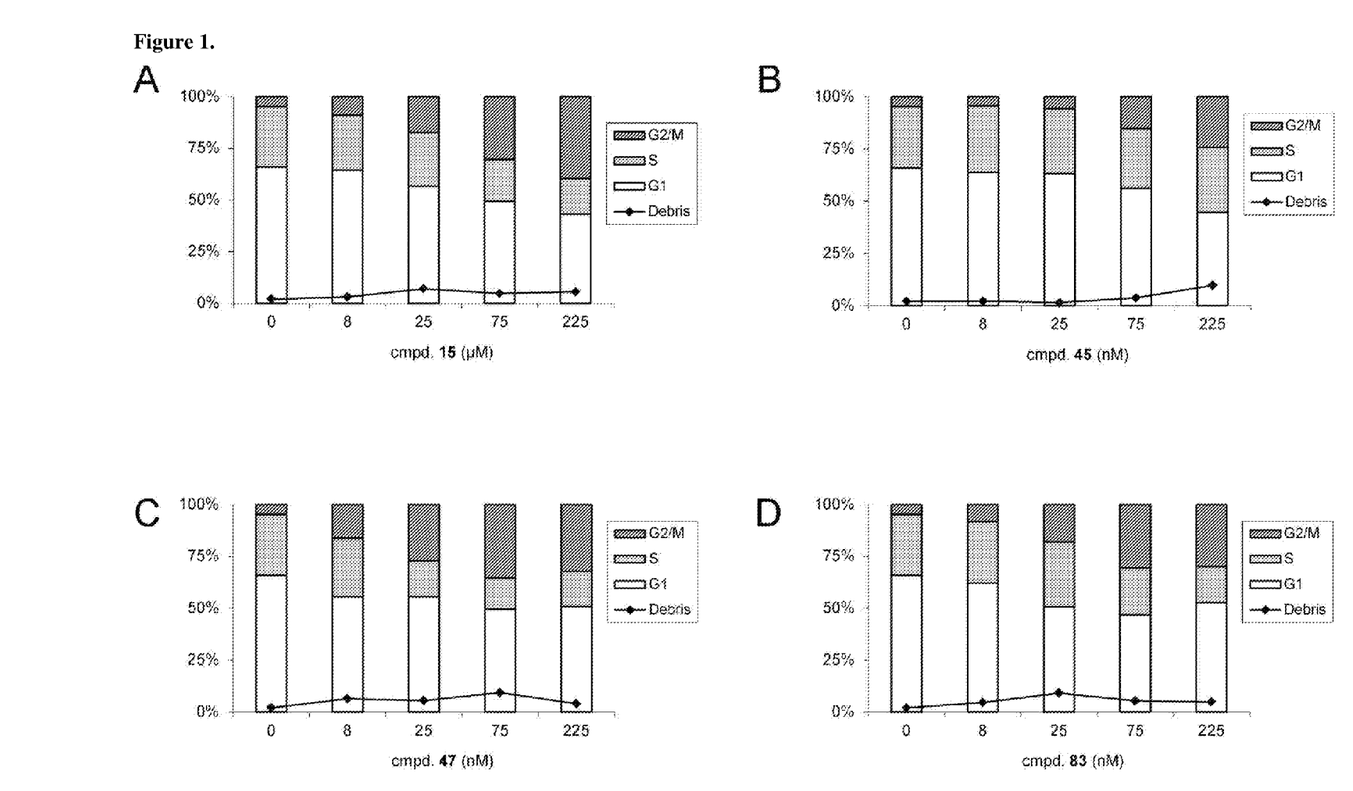

Sub-confluent cells were treated with test compounds at different concentrations for 24 h. The cultures were pulse-labeled with 10 mM 5-bromo-20-deoxyuridine (BrdU) for 30 min at 37° C. prior to harvesting. The cells were then washed in PBS, fixed with 70% ethanol, and denatured in 2 M HCl. Following neutralization, the cells were stained with anti-BrdU fluorescein-labeled antibodies, washed, stained with propidium iodide and analyzed by flow cytometry using a 488 nm laser The antiproliferative activity of compounds 15, 45, 47 and 84 was measured in an asynchronously growing breast carcinoma cell line MCF7. As shown in FIG. 1, the compounds potently arrested cells in S, G2 and M phases.

Example 21

Novel Compounds Activate Caspases 3 and 7 in Cancer Cells

Measurement of proapoptotic properties of new compounds was based on quantification of enzymatic activities of caspases-3/7. Activity of cellular caspase-3/7 was measured according to Carrasco et al., 2003, BioTechniques, 34(5): 1064-67. Briefly, the cells were incubated in a 96-well plate overnight. Next day, the compounds in appropriate concentrations were added and cells were incubated for 24 hours. After incubation, 3× caspase-3/7 assay buffer (150 mM HEPES pH 7.4, 450 mM NaCl, 150 mM KCl, 30 mM MgCl$_2$, 1.2 mM EGTA, 1.5% Nonidet P40, 0.3% CHAPS, 30% sucrose, 30 mM DTT, 3 mM PMSF) with 150 μM Ac-DEVD-AMC as a substrate (Sigma-Aldrich) was added to the wells and plates were incubated at 37° C. at room temperature. The caspase activity was measured using Fluoroskan Ascent microplate reader (Labsystems) at 346 nm/442 nm (excitation/emission).

Figure 2:
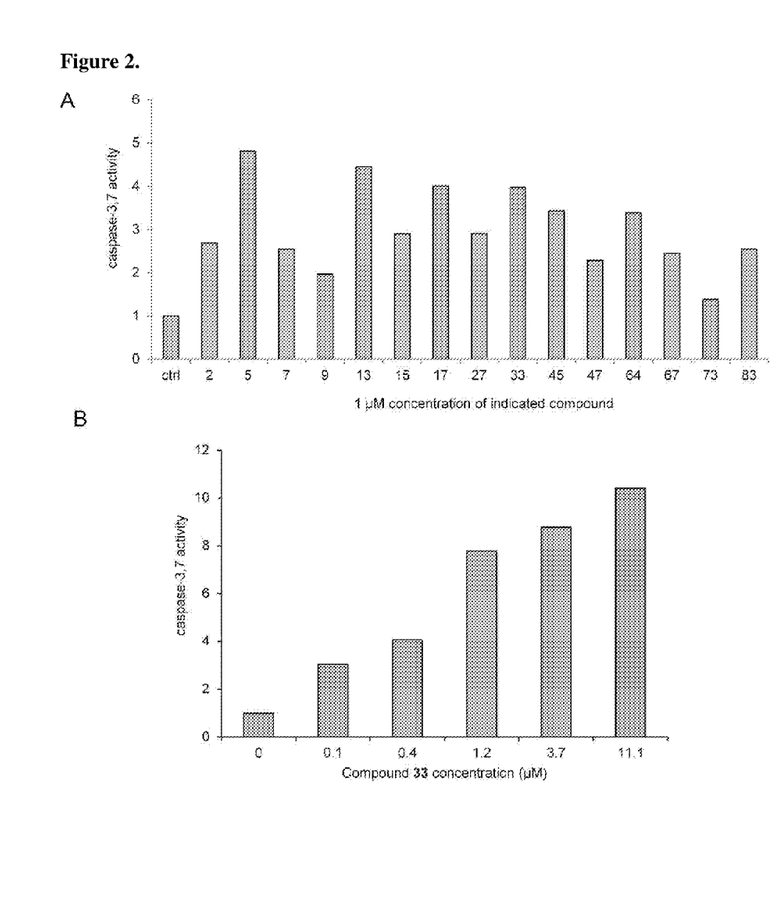

A fluorimetry-based caspase-3/7 activity assay in K562 cells revealed strong proapoptotic activity of most novel compounds compared with control, untreated cells (FIG. 2A).

In next experiment, compound 33 was selected for determination of caspase activation in K562 cell line. A fluorimetry-based caspase-3/7 activity assay in K562 cells treated with compound 33 revealed potent dose-dependent activation of the caspases in nanomolar concentrations (FIG. 2B).

Figure 3:
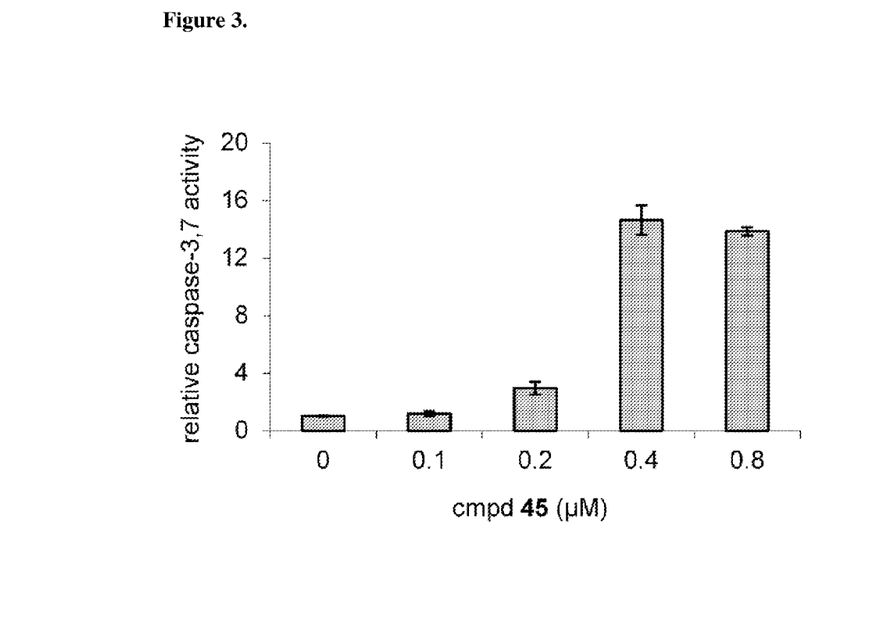
FIG. 3 shows the effect of compound 45 on apoptosis in HCT116 cells. Activities of caspases 3 and 7 were assayed in lysed HCT116 cells treated for 24 h with various doses of compound 45.

In next experiment, compound 45 was selected for determination of caspase activation in a colon carcinoma cell line HCT116. A fluorimetry-based caspase-3/7 activity assay in HCT116 cells treated with compound 45 revealed potent dose-dependent activation of the caspases in nanomolar concentrations (FIG. 3).

Example 22

Novel Compounds Downregulate Antiapoptotic Proteins in Treated Cancer Cells

Effect of novel compounds on apoptosis was confirmed by immunoblotting analysis of selected apoptotic proteins. For immunoblotting, cell were harvested, washed three times with ice-cold PBS and lysed in a buffer (50 mM Tris, pH 7.4, 250 mM NaCl, 5 mM EDTA, 50 mM NaF, 1 mM Na$_3$VO$_4$, 1% Nonidet P40) containing mixture of protease and phosphatase inhibitors (Sigma-Aldrich). 20 μg of total proteins were separated by SDS-polyacrylamide gel electrophoresis (SDS-PAGE) and transferred onto nitrocellulose membranes. Membranes were blocked in 5% milk and 0.1% Tween 20 in PBS and probed overnight with specific antibodies. Specific antibodies were purchased from SigmaAldrich (anti a-tubulin, clone DM1A), Santa Cruz Biotechnology (anti-Mcl-1, clone S-19; anti-PARP, clone F-2; anti-Mdm-2, clone SMP14; anti-Bcl-2), DAKO Cytomation Cell Signaling (anti-PUMA) or were a generous gift from Dr. B. Vojtesek (anti-p53, clone DO-1). All primary antibodies were diluted in PBS containing 5% powdered milk; 0.1% Tween 20. Peroxidase conjugated rabbit anti-mouse immunoglobulin or porcine anti-rabbit immunoglobulin antisera (DAKO) were used as the secondary antibodies and visualised with ECL reagents (GE-Healthcare Life Sciences).

Figure 4:
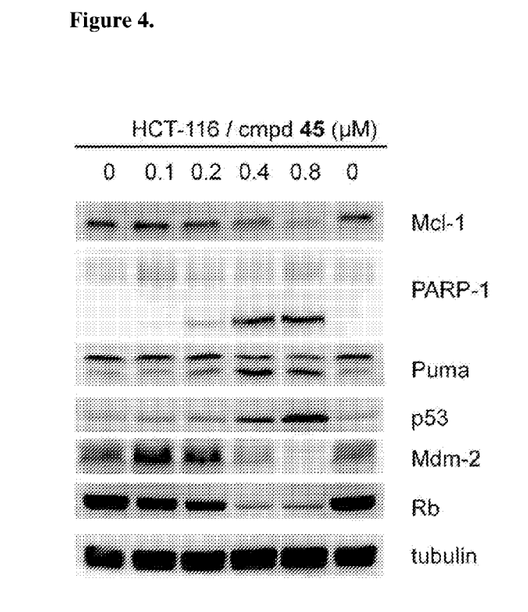
FIG. 4 shows immunoblotting analysis of several apoptotic markers in HCT116 cells treated with compound 45 for 24 hours.

The results of an immunoblotting analysis of several proteins involved in apoptotic cell death are shown in FIG. 4. An appearance of the caspase-3-cleaved PARP-1 fragment at 89 kDa after cell exposure to compound 45 was observed in treated HCT116 cells and was and markedly associated with a diminution of its fulllength form. The activation of mitochondrial apoptosis was evident also from determination of the level of anti-apoptotic protein Mcl-1 that showed a dose-dependent decrease. Compound 45 also rapidly increased the expression of tumor suppressor protein p53, which is known to be involved in regulation of apoptosis. This increase was accompanied by decreased expression of Mdm-2, which is a negative regulator of p53.

Example 23

Anti-Vascularisation Effects of Novel Compounds

To verify that novel compounds have anti-vascularisation properties, we analyzed their influence on the proliferation and migration of HUVECs. HUVECs (human umbilical vein endothelial cells) were purchased from Promocell (Heidelberg, Germany) and cultured in endothelial cell growth medium (ECGM, Promocell, Heidelberg, Germany) containing 10% FCS (Biochrom, Berlin, Germany). Experiments were performed using cells at passage 3.

For proliferation assay, $1.5 \times 10^3$ HUVECs were cultured for 24 h. Afterwards, cells were either left untreated or treated with novel compounds for 72 h. Proliferation assay was performed using crystal violet as described previously (Koltermann et al. 2007, Cell Mol. Life Sci. 64:1715-1722).

For migration assay, confluent HUVECs were scratched with a pipette tip and immediately treated with either starvation medium M199 (serum-free, negative control; PAN Biotech) or full endothelial cell growth medium (positive control). After 16 h, cells were fixed with 3% formaldehyde and images were taken using the TILLvisON system (Lochham, Germany) connected to an Axiovert 200 microscope (Zeiss, Germany). Evaluation of pictures was made by S.CO LifeScience (Garching, Germany). Migration was quantified as the ratio of the area covered with cells and the area of the cell free wound.

TABLE 5

Anti-vascularisation effects of novel compounds.

| Compound | Inhibition of proliferation (EC50) | Inhibition of migration (EC50) |
|---|---|---|
| 5 | 234 nM | |
| 7 | 648 nM | 550 nM |
| 8 | 569 nM | |
| 9 | 136 nM | |
| 13 | 9 nM | 26 nM |
| 15 | 153 nM | |
| 17 | 95 nM | |
| 27 | 33 nM | 35 nM |
| 33 | 14 nM | 22 nM |
| 45 | 176 nM | 500 nM |
| 47 | 181 nM | |
| 65 | 5 nM | 77 nM |
| 67 | 69 nM | |
| 73 | 2.278 µM | |
| 81 | 1.331 µM | |
| 83 | 34 nM | 39 nM |

The example results are summarized in Table 5. Tested compounds significantly reduced HUVECs' proliferation and in nanomolar concentrations. Importantly, the effect was purely antiproliferative, with only marginal cytotoxicity. In addition, the migration of VEGF-stimulated HUVECs across a scratched area was inhibited by novel compounds in a dose-dependent manner; significant inhibition of migration was observed at nanomolar concentrations.

Example 24

Dry Capsules 5000 capsules, each of which contains 0.25 g of one of the compounds of the formula I mentioned in the preceding or following Examples as active ingredient, are prepared as follows:
Composition

| | |
|---|---|
| Active ingredient | 1250 g |
| Talc | 180 g |
| Wheat starch | 120 g |
| Magnesium stearate | 80 g |
| Lactose | 20 g |

Preparation Process:
The powdered substances mentioned are pressed through a sieve of mesh width 0.6 mm. Portions of 0.33 g of the mixture are transferred to gelatine capsules with the aid of a capsule-filling machine.

Example 25

Soft Capsules 5000 soft gelatine capsules, each of which contains 0.05 g of one of the compounds of the formula I mentioned in the preceding or following Examples as active ingredient, are prepared as follows:
Composition

| | |
|---|---|
| Active ingredient | 250 g |
| Lauroglycol | 2 litres |

Preparation Process:
The powdered active ingredient is suspended in Lauroglykol® (propylene glycol laurate, Gattefossé S.A., Saint Priest, France) and ground in a wet-pulveriser to a particle size of about 1 to 3 µm. Portions of in each case 0.419 g of the mixture are then transferred to soft gelatine capsules by means of a capsule-filling machine.

Example 26

Soft Capsules 5000 soft gelatine capsules, each of which contains 0.05 g of one of the compounds of the formula I mentioned in the preceding or following Examples as active ingredient, are prepared as follows:
Composition

| | |
|---|---|
| Active ingredient | 250 g |
| PEG 400 | 1 litre |
| Tween 80 | 1 litre |

Preparation Process:
The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

The invention claimed is:
1. 5-Substituted 7-[4-(2-pyridyl)phenylmethylamino]-3-isopropylpyrazolo[4,3-d]pyrimidine of general formula I wherein,
R is selected from the group containing
heterocycloalkyl, which is a $C_3$-$C_{10}$ cycloalkyl group wherein one or more, of the ring carbons is/are replaced with a heteroatom selected from N, O, S, said heterocycloalkyl group being optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl, and amino substituents;
heterocycloalkyl alkyl, which is a $C_3$-$C_{10}$ cycloalkyl group wherein one or more, of the ring carbons is/are replaced with a heteroatom selected from N, O, S, bound via a $C_1$-$C_4$ alkylene spacer, said heterocycloalkyl alkyl group being optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl and amino substituents;
R'—X
wherein X is selected from —NH— and —N($C_1$-$C_8$ alkyl)-moiety, and
R' is selected from
$C_2$-$C_{10}$ linear or branched alkyl, optionally substituted by at least one substituent selected from hydroxy and amino substituents;
(dialkylamino)alkyl group wherein the alkyls are independently selected from $C_1$-$C_{10}$ linear or branched alkyl;
$C_3$-$C_{10}$ cycloalkyl, which is a cyclic or polycyclic alkyl group containing 3 to 10 carbon atoms, optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl and amino substituents;
heterocycloalkyl, which is a $C_3$-$C_{10}$ cycloalkyl group wherein one or more, of the ring carbons is/are replaced with a heteroatom selected from N, O, S, said heterocycloalkyl group being optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl and amino substituents;
heterocycloalkyl alkyl, which is a $C_3$-$C_{10}$ cycloalkyl group wherein one or more, of the ring carbons is/are replaced with a heteroatom selected from N, O, S, bound via a $C_1$-$C_4$ alkylene spacer, said heterocycloalkyl alkyl group being optionally substituted independently at each occurrence by at least one substituent selected from the group consisting of hydroxy, $C_1$-$C_4$ alkyl, $C_1$-$C_4$ alkoxy, $C_1$-$C_4$ hydroxyalkyl and amino substituents;
benzyl group, optionally substituted independently at each occurrence by at least one substituent selected from the group consisting of fluoro, chloro, hydroxy, $C_1$-$C_4$ alkyl, $C_1$-$C_4$ alkoxy, $C_1$-$C_4$ hydroxyalkyl and amino substituents;
and pharmaceutically acceptable salts thereof, or addition salts with acids.

2. 5-Substituted 7-[4-(2-pyridyl)phenylmethylamino]-3-isopropylpyrazolo[4,3-d]pyrimidines of general formula I wherein,
R is selected from the group containing
methylsulfonyl, N-morpholinyl, N-pyrrolidinyl, N-pyrazolidinyl, N-imidazolidinyl, N-piperazinyl, N-piperidinyl, N-thiomorpholinyl, 4-methylpiperazin-1-yl, 4-(2-hydroxyethyl)piperazinyl, (R)-(2-hydroxymethylpyrrolidine-1-yl), ethylamino, propylamino, butylamino, (2-hydroxyethyl)amino, (3-hydroxypropyl)amino, 2(R)-hydroxypropylamino, 2(S)-hydroxypropylamino, 4-hydroxybut-2(R)-ylamino, 4-hydroxybut-2(S)-ylamino, 4-hydroxybut-2(R,S)-ylamino, 2-(hydroxy-2-methyl)propylamino, (2,3-dihydroxypropyl)amino, (1-hydroxy-3-methylbutyl)amino, [(R,S)-(2-hydroxypent-3-yl)]amino, [(R)-(2-hydroxypent-3-yl)]amino, [(S)-(2-hydroxypent-3-yl)]amino, (R)-[1-isopropyl-2-hydroxyethyl]amino, (S)-[1-isopropyl-2-hydroxyethyl]amino, (2-aminoethyl)amino, (3-aminopropyl)amino, (4-aminobutyl)amino, (5-aminopentyl)amino, (6-aminohexyl)amino, [3-amino-2-hydroxypropyl]amino, [1-(dimethylamino)methyl]amino, [2-(dimethylamino)ethyl]amino, [3-(dimethylamino)propyl]amino, [4-(dimethylamino)butyl]

amino, [2-(diethylamino)ethyl]amino, [3-(diethylamino)propyl]amino, (aziridin-1-yl)ethylamino, (azolidin-1-yl)ethylamino, (azetidin-1-yl)ethylamino, (piperidin-1-)ethylamino, (azetidin-1-yl)ethylamino, (azetidin-1-yl)propylamino, cyclopropylamino, cyclobutylamino, cyclopentylamino, cyclohexylamino, (cis-2-aminocyclohexyl)amino, (trans-2-aminocyclohexyl)amino, (cis,trans-2-aminocyclohexyl)amino, (cis,trans-3-aminocyclohexyl)amino, (trans-4-aminocyclohexyl)amino, (cis-4-aminocyclohexyl)amino, (cis,trans-4-aminocyclohexyl)amino, (cis-2-hydroxycyclohexyl)amino, (trans-2-hydroxycyclohexyl)amino, (cis,trans-2-hydroxycyclohexyl)amino, (cis,trans-3-hydroxycyclohexyl)amino, (trans-4-hydroxycyclohexyl)amino, (cis-4-hydroxycyclohexyl)amino, (cis,trans-4-hydroxycyclohexyl)amino, (2-methoxybenzyl)amino, (3-methoxybenzyl)amino, (4-methoxybenzyl)amino, (3,5-dimethoxybenzyl)aminoe, (2,6-dimethoxybenzyl)amino, (3,4,5-trimethoxybenzyl)amino, (2,4,6-trimethoxybenzyl)amino, (2-fluorobenzyl)amino, (3-fluorobenzyl)amino, (4-fluorobenzyl)amino, (2-chlorobenzyl)amino, (3-chlorobenzyl)amino, (4-chlorobenzyl)amino, (2,4-dichlorobenzyl)amino, (3,4,5-trichlorobenzyl)amino.

3. 5-Substituted 7-[4-(2-pyridyl)phenylmethylamino]-3-isopropylpyrazolo[4,3-d]pyrimidines of the general formula I according to claim 1 for use in a method of inhibiting endothelial cell migration.

4. 5-Substituted 7-[4-(2-pyridyl)phenylmethylamino]-3-isopropylpyrazolo[4,3-d]pyrimidines of the general formula I according to claim 1 for use for inhibition of CDK5.

5. 5-Substituted 7-[4-(2-pyridyl)phenylmethylamino]-3-isopropylpyrazolo[4,3-d]pyrimidines of the general formula I according to claim 1 for use in a method of treatment of cancer disorders related to the inhibition of CDK5.

6. 5-Substituted 7-[4-(2-pyridyl)phenylmethylamino]-3-isopropylpyrazolo[4,3-d]pyrimidines of the general formula I according to claim 1 for use in a method of treatment of a disorder selected from leukemia or solid tumors related to the inhibition of CDK5.

7. 5-Substituted 7-[4-(2-pyridyl)phenylmethylamino]-3-isopropylpyrazolo[4,3-d]pyrimidines of the general formula I according to claim 1 for use in a method of inhibition and/or treatment of vascularization during cancer, embryonic development, menstruation cycle and wound healing.

8. A pharmaceutical composition, characterized in that it comprises at least one 5-substituted 7-[4-(2-pyridyl)phenylmethylamino]-3-isopropylpyrazolo [4,3-d]pyrimidine of the general formula I according to claim 1, and at least one pharmaceutically acceptable carrier.

\* \* \* \* \*

UNITED STATES PATENT AND TRADEMARK OFFICE
CERTIFICATE OF CORRECTION

PATENT NO. : 9,957,273 B2
APPLICATION NO. : 15/558151
DATED : May 1, 2018
INVENTOR(S) : Libor Havlicek et al.

Page 1 of 1

It is certified that error appears in the above-identified patent and that said Letters Patent is hereby corrected as shown below:

On the Title Page

(73) Assignee should read: USTAV EXPERIMENTALNI
BOTANIKY AV CR, V.V.I., Prague (CZ)
PALACKY UNIVERSITY OLOMOUC, Olomouc (CZ)

Signed and Sealed this
Twentieth Day of August, 2019

Andrei Iancu
*Director of the United States Patent and Trademark Office*